US010018633B2

(12) United States Patent
Zu

(10) Patent No.: US 10,018,633 B2
(45) Date of Patent: Jul. 10, 2018

(54) MULTI-APTAMER-BASED, CELL-SPECIFIC, ONE-STEP TUMOR CELL DETECTION ASSAYS

(71) Applicant: The Methodist Hospital Research Institute, Houston, TX (US)

(72) Inventor: Youli Zu, Bellaire, TX (US)

(73) Assignee: The Methodist Hospital Research Institute, Houston, TX (US)

(*) Notice: Subject to any disclaimer, the term of this patent is extended or adjusted under 35 U.S.C. 154(b) by 259 days.

(21) Appl. No.: 14/738,337

(22) Filed: Jun. 12, 2015

(65) Prior Publication Data

US 2015/0276750 A1 Oct. 1, 2015

Related U.S. Application Data

(63) Continuation of application No. PCT/US2013/074797, filed on Dec. 12, 2013.

(60) Provisional application No. 61/801,523, filed on Mar. 15, 2013, provisional application No. 61/736,452, filed on Dec. 12, 2012.

(51) Int. Cl.
| | |
|---|---|
| G01N 33/574 | (2006.01) |
| C12Q 1/6816 | (2018.01) |
| C12Q 1/6886 | (2018.01) |
| G01N 33/53 | (2006.01) |
| G01N 33/542 | (2006.01) |

(52) U.S. Cl.
CPC ..... *G01N 33/57492* (2013.01); *C12Q 1/6816* (2013.01); *C12Q 1/6886* (2013.01); *G01N 33/5308* (2013.01); *G01N 33/542* (2013.01); *G01N 2333/70578* (2013.01)

(58) Field of Classification Search
None
See application file for complete search history.

(56) References Cited

U.S. PATENT DOCUMENTS

| | | |
|---|---|---|
| 6,680,377 B1 | 1/2004 | Stanton et al. |
| 2004/0241758 A1 | 12/2004 | Goodwin et al. |
| 2009/0130650 A1 | 5/2009 | Tan et al. |
| 2010/0266496 A1* | 10/2010 | Hansen ............ A61K 39/395 424/1.49 |
| 2012/0219961 A1 | 8/2012 | Bruno et al. |

FOREIGN PATENT DOCUMENTS

| | | |
|---|---|---|
| EP | 1972693 | 9/2008 |
| WO | WO 2010/056337 | 5/2010 |

OTHER PUBLICATIONS

Allard, W. Jeffrey et al., "Tumor cells circulate in the peripheral blood of all major carcinomas but not in healthy subjects or patients with nonmalignant diseases," *Clin. Cancer Res.*, 10(20):6897-6904 (Oct. 15, 2004).
Alunni-Fabbroni, Marianna and Sandri, Maria Teresa, "Circulating tumour cells in clinical practice: methods of detection and possible characterization," *Methods*, 50(4):289-297 (Jan. 2010).
Attard, Gerhardt et al., "Characterization of ERG, AR and PTEN gene status in circulating tumor cells from patients with castration-resistant prostate cancer," *Cancer Res.*, 69:(7):2912-2918 (Apr. 1, 2009).
Balasubramanian, P et al., "Confocal images of circulating tumor cells obtained using a methodology and technology that removes normal cells," *Mol. Pharm.*, 6(5):1402-1408 (2009).
Blank, Michael and Blind, Michael, "Aptamers as tools for target validation," *Curr. Opin. Chem. Biol.*, 9(4):336-342 (2005).
Bunka, David H. and Stockley, Peter G., "Aptamers come of age—at last," *Nat. Rev. Microbiol.*, 4(8):588-596 (Aug. 2006).
Burke, Donald H. et al., "RNA aptamers to the adenosine moiety of S-adenosyl methionine: structural inferences from variations on a theme and the reproducibility of SELEX," *Nucleic Acids Res.*, 25(10):2020-2024 (May 15, 1997).
Carlson, Bob "Aptamers: the new frontier in drug development?" *Biotechnol. Healthcare*, 4(2):31-32, 3436 (Apr. 2007).
Cerchia, Laura et al., "Nucleic acid aptamers in cancer medicine," *FEBS Lett.*, 528(1-3):12-16 (Aug. 2002).
Cristofanilli, Massimo et al., "Circulating tumor cells, disease progression, and survival in metastatic breast cancer," *N. Eng. J. Med.*, 351(8):781-791 (Aug. 19, 2004).
Davis, Kenneth A. et al., "Staining of cell surface human CD4 with 2'-F-pyrimidine-containing RNA aptamers for flow cytometry," *Nucleic Acids Res.*, 26(17):3915-3924 (Jul. 21, 1998).
Ellington, Andrew D. and Szostak, Jack W., "In vitro selection of RNA molecules that bind specific ligands," *Nature*, 346(6287):818-822 (Aug. 30, 1990).
Gascoyne, Peter R.C. et al., "Isolation of rare cells from cell mixtures by dielectrophoresis," *Electrophoresis*, 30(8):1388-1398 (Apr. 30, 2009).
Han, Kun et al., "Design strategies for aptamer-based biosensors," *Sensors*, 10(5):4541-4557 (May 4, 2010).
Hermann, Thomas and Patel, Dinshaw J., "Adaptive recognition by nucleic acid aptamers," *Science*, 287(5454):820-825 (Feb. 2000).
Heyduk, Tomasz and Heyduk, Ewa, "Molecular beacons for detecting DNA binding proteins," *Nat. Biotechnol.*, 20(2):171-176 (Feb. 2002).
Huang, Chao-June et al., "Integrated microfluidic system for rapid screening of CRP aptamers utilizing systematic evolution of ligands by exponential enrichment (SELEX)," *Biosens. Bioelectron.*, 25(7):1761-1766 (Mar. 2010).

(Continued)

*Primary Examiner* — James Martinell
(74) *Attorney, Agent, or Firm* — Haynes and Boone, LLP

(57) ABSTRACT

Disclosed are methods and compositions for the detection of one or more different types of cellular biomarkers in a biological sample, and in particular, methods and compositions for the rapid, one-step, highly-cell specific detection of circulating tumor cells from minute quantities of mammalian biological fluids, including, for example, from a single drop of human blood. In certain embodiments, distinctly-labeled, multi-aptamer detection reagents are provided for detecting and quantitating selected cancer cells in clinical samples such as patient specimens and/or tissues. Aptamer-based imaging methodologies are also provided for use in a variety of diagnostic assay protocols.

28 Claims, 25 Drawing Sheets

(56) References Cited

OTHER PUBLICATIONS

Jarosch, Florian et al., "In vitro selection using a dual RNA library that allows primerless selection," Nucleic Acids Res., 34(12):e86, 9 pages (Jul. 19, 2006).

Jayasena, Sumedha D. "Aptamers: an emerging class of molecules that rival antibodies in diagnostics," Clin. Chem., 45(9):1628-1650 (Sep. 1999).

Juskowiak, Bernard "Nucleic acid-based fluorescent probes and their analytical potential," Anal. Bioanal. Chem., 399(9):3157-3176 (Mar. 2011).

Liu, MC et al., "Circulating tumor cells: a useful predictor of treatment efficacy in metastatic breast cancer," J. Clin. Oncol., 27(31):5153-5159 (Nov. 1, 2009).

López-Colón, Dalia et al., "Aptamers: turning the spotlight on cells," Nanomed. Nanobiotechnol., 3(3):328-340 (May-Jun. 2011).

Lou, Kai-Jye, "Imaging with aptamers," SciBX, 4(11): 1-2; Nature Publishing Group (Mar. 17, 2011).

Lu, Janice et al., "Isolation of circulating epithelial and tumor progenitor cells with an invasive phenotype from breast cancer patients," Int. J. Cancer, 126(3):669-683 (Feb. 2010).

Maheswaran, Shyamala et al., "Detection of mutations in EGFR in circulating lung-cancer cells," N. Engl. J. Med., 359(4):366-377 (Jul. 24, 2008).

Mairal, Teresa et al., "Aptamers: molecular tools for analytical applications," Anal. Bioanal. Chem., 390(4):989-1007 (Feb. 2008).

Miller, M. Craig et al., "Significance of circulating tumor cells detected by the CellSearch system in patients with metastatic breast colorectal and prostate cancer," J. Oncol., 2010:617421, 8 pages. (Dec. 9, 2009).

Mori, Tadashi et al., "RNA aptamers selected against the receptor activator of NF-$_k$B acquire general affinity to proteins of the tumor necrosis factor receptor family," Nucleic Acids Res., 32(20):6120-6128 (Nov. 23, 2004).

Nagrath, Sunitha et al., "Isolation of rare circulating tumour cells in cancer patients by microchip technology," Nature, 450(7173):1235-1239 (Dec. 27, 2007).

Oliphant, Arnold R. et al., "Defining the sequence specificity of DNA-binding proteins by selecting binding sites from random-sequence oligonucleotides: analysis of yeast GCN4 protein," Molec. Cell. Biol., 9(7): 2944-2949 (Jul. 1989).

Paris, PL et al., "Functional phenotyping and genotyping of circulating tumor cells from patients with castration resistant prostate cancer," Cancer Lett., 277(2):164-173 (May 2009).

Rao, DD et al., "siRNA vs. shRNA: similarities and differences," Adv. Drug. Deliv. Rev., 61(9):746-759 (Jul. 2009).

Riethdorf, S et al., "Detection of circulating tumor cells in peripheral blood of patients with metastatic breast cancer: a validation study of the cell search system," Clin. Cancer Res., 13(3):920-928 (Feb. 1, 2007).

Sefah, K et al., "Development of DNA aptamers using Cell-SELEX," Nat. Protoc., 5(6):1169-1185 (Jun. 2010).

Sequist, LV et al., "The CTC-chip: an exciting new tool to detect circulating tumor cells in lung cancer patients," J. Thorac. Oncol., 4(3):281-283 (Mar. 2009).

Shangguan, D et al., "Aptamers evolved from live cells as effective molecular probes for cancer study," Proc. Nat'l. Acad. Sci. USA, 103(32):11838-11843 (Aug. 8, 2006).

Shi, H et al., "Activatable aptamer probe for contrast-enhanced in vivo cancer imaging based on cell membrane protein-triggered conformation alteration," Proc. Nat'l. Acad. Sci. USA, 108(10):3900-3905 (Mar. 8, 2011).

Stoltenburg, R et al., "SELEX—a (r)evolutionary method to generate high-affinity nucleic acid ligands," Biomol. Eng., 24(4):381-403 (Oct. 2007).

Stott, S et al., "Isolation of circulating tumor cells using a microvortex-generating herringbone-chip," Proc. Nat'l. Acad. Sci. USA, 107(43):18392-18397 (Oct. 26, 2010).

Swennenhuis, JF et al., "Characterization of circulating tumor cells by fluorescence in situ hybridization," Cytometry (Part A): J. Int. Soc. Adv. Cytometry, 75A:520-527 (Mar. 16, 2009).

Talasaz, AH et al., "Isolating highly enriched populations of circulating epithelial cells and other rare cells from blood using a magnetic sweeper device," Proc. Nat'l. Acad. Sci. USA, 106(10):3970-3975 (Mar. 10, 2009).

Tan, W et al., "Molecular beacons: a novel DNA probe for nucleic acid and protein studies," Chemistry, 6(7):1107-1111 (Apr. 2000).

Tuerke, Craig et al., "Systematic evolution of ligands by exponential enrichment: RNA ligands to bacteriophage T4 DNA polymerase," Science, 249(4968):505-510 (Aug. 3, 1990).

Ulrich, H and Wrenger, C, "Disease-specific biomarker discovery by aptamers," Cytometry (Part A): J. Int. Soc. Adv. Cytometry, 75A:727-733 (Jun. 29, 2009).

Wu, CCN et al., "Selection of oligonucleotide aptamers with enhanced uptake and activation of human leukemia B cells," Hum. Gene Ther., 14:849-860 (Jun. 10, 2003).

Weight, RM et al., "Detection of circulating melanoma cells in human blood using photoacoustic flowmetry," Conf. Proc. IEEE Eng. Med. Biol. Soc., 2009:106-109 (2009).

Product Profile: "Fluorescent Molecular Probes," PG-MB-V4.1, GeneLink, Inc., Hawthorne, NY, USA, 2014, (19 pages).

Yang, L et al., "Optimization of an enrichment process for circulating tumor cells from the blood of head and neck cancer patients through depletion of normal cells," Biotechnol. Bioeng., 102(2):521-534 (Feb. 1, 2009).

Zeng, Z et al., "Using oligonucleotide aptamer probes for immunostaining of formalin-fixed and paraffin-embedded tissues," Modern Pathol., 23(12):1553-1558 (Dec. 2010).

Zhang, P et al., "Combination of an aptamer probe to CD4 and antibodies for multicolored cell phenotyping," Am. J. Clin.I Pathol., 134:586-593 (2010).

Zhang, P et al., "Using an RNA aptamer probe for flow cytometry detection of CD30-expressing lymphoma cells," Lab. Investig., 89(12):1423-1432 (Dec. 2009).

Zhao, N et al., "A nanocomplex that is both tumor cell-selective and cancer gene-specific for anaplastic large cell lymphoma," J. Nanobiotechnol., 9(2):1-12 (2011).

International Search Report and Written Opinion dated Feb. 5, 2014 issued in PCT/US2013/074797 filed on Dec. 12, 2013 (8 pages).

Brody, Edward N. and Gold, Larry, "Aptamers as therapeutic and diagnostic agents," J. Biotechnol., 74(1):5-13 (2000).

Tyagi, Sanjay et al., "Molecular beacons: probes that fluoresce upon hybridization," Nature Biotechnol., 14(XX):303-308 (Mar. 1996).

\* cited by examiner

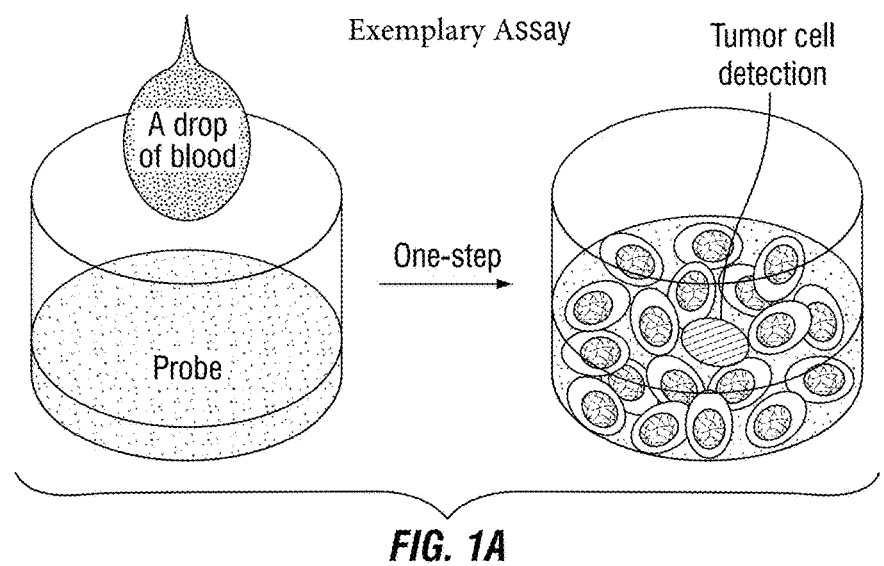
*FIG. 1A*
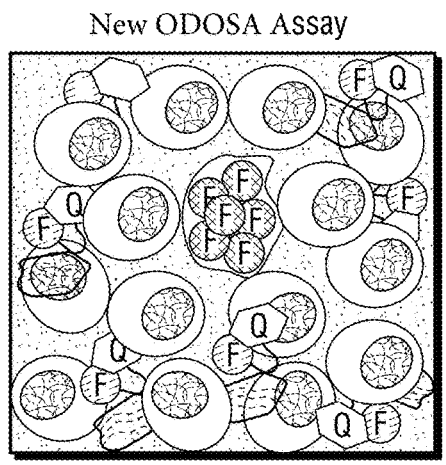
*FIG. 1B*
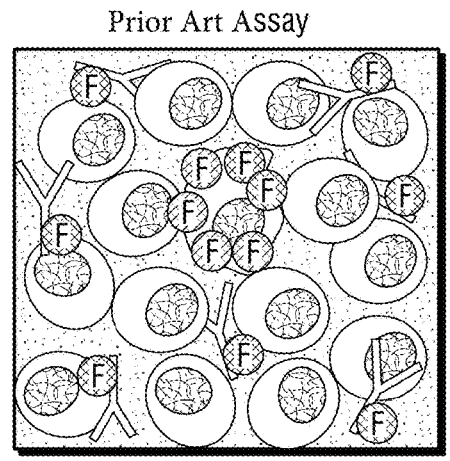
*FIG. 1C*
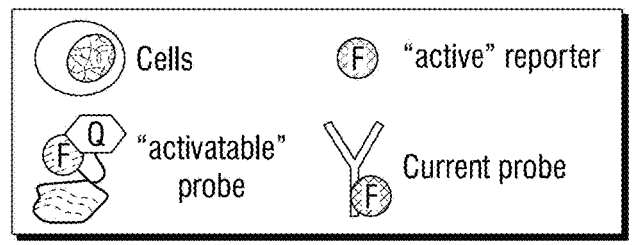

Aptamer probe

Alexa 488 membrane stain

Merged Aptamer and Alexa 488

Light microscopy

Light Field

Antibody-FITC

Aptamer-Cy3

Merged FITC and Cy3

Develop the tumor cell-specific aptamer probes that contain an "activatable" reporter system Mix patient's blood specimens with the inactive aptamer probes Activation of aptamer probes exclusively within the circulating tumor cells

*(SEQ ID NO: 1)*

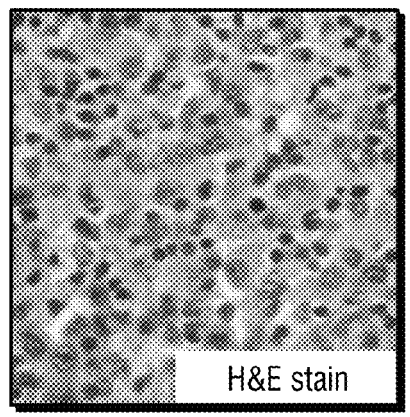
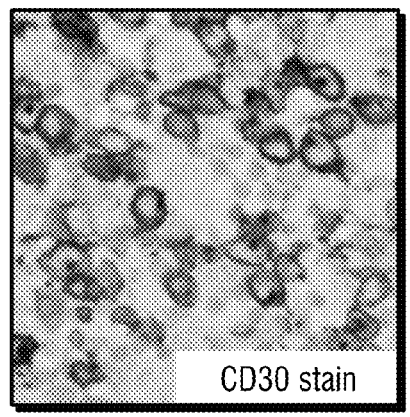
*FIG. 20A*  *FIG. 20B*
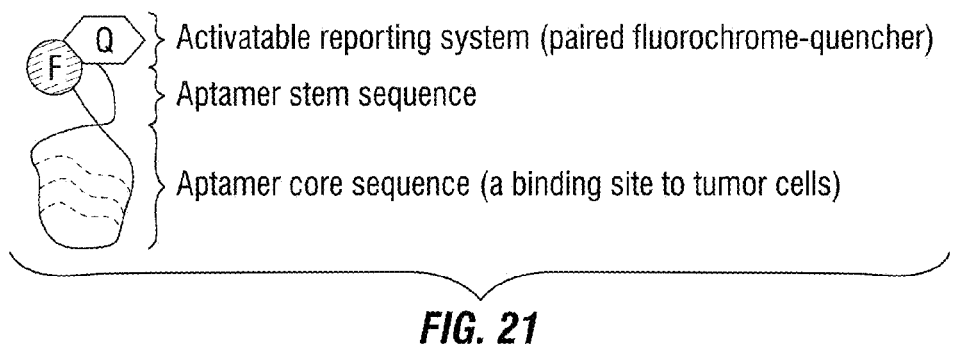
*FIG. 21*
| Fluorochromes | Quenchers |
|---|---|
| 1. 6-Fam | Dabcyl |
| 2. HEX | BHQ-1 |
| 3. TAMRA | BHQ-2 |
| 4. Cy3 | Cy5Q |
| 5. Cy5.5 | BHQ-3 |
| 6. Cy7 | Cy7Q |
| 7. CW-800 | QC-1 |
*FIG. 22*

SEQUENCE LISTING

```
<160> NUMBER OF SEQ ID NOS: 11

<210> SEQ ID NO 1
<211> LENGTH: 39
<212> TYPE: RNA
```

<213> ORGANISM: Artificial Sequence
<220> FEATURE:
<223> OTHER INFORMATION: Synthetic Probe

<400> SEQUENCE: 1
gauucguaug gguggaucg ggaagggcua cgaacaccg          39

<210> SEQ ID NO 2
<211> LENGTH: 34
<212> TYPE: RNA
<213> ORGANISM: Artificial Sequence
<220> FEATURE:
<223> OTHER INFORMATION: Synthetic Probe

<400> SEQUENCE: 2
auucguaugg gugggaucgg gaagggcuac gaac             34

<210> SEQ ID NO 3
<211> LENGTH: 38
<212> TYPE: RNA
<213> ORGANISM: Artificial Sequence
<220> FEATURE:
<223> OTHER INFORMATION: Synthetic Probe

<400> SEQUENCE: 3
ggauucguau gggugggauc gggaagggcu acgaacac        38

<210> SEQ ID NO 4
<211> LENGTH: 42
<212> TYPE: RNA
<213> ORGANISM: Artificial Sequence
<220> FEATURE:
<223> OTHER INFORMATION: Synthetic Probe

<400> SEQUENCE: 4
auggauucgu auggguggga ucgggaaggg cuacgaacac cg    42

<210> SEQ ID NO 5
<211> LENGTH: 46
<212> TYPE: RNA
<213> ORGANISM: Artificial Sequence
<220> FEATURE:
<223> OTHER INFORMATION: Synthetic Probe

<400> SEQUENCE: 5
caauggauuc guaugggugg gaucgggaag ggcuacgaac accgua   46

<210> SEQ ID NO 6
<211> LENGTH: 50
<212> TYPE: RNA
<213> ORGANISM: Artificial Sequence
<220> FEATURE:
<223> OTHER INFORMATION: Synthetic Probe

<400> SEQUENCE: 6
cacaauggau ucguaugggu gggaucggga agggcuacga acaccguaac   50

<210> SEQ ID NO 7
<211> LENGTH: 54
<212> TYPE: RNA
<213> ORGANISM: Artificial Sequence
<220> FEATURE:
<223> OTHER INFORMATION: Synthetic Probe

<400> SEQUENCE: 7
gacacaaugg auucguaugg gugggaucgg gaagggcuac gaacaccgua acgg   54

```
<210> SEQ ID NO 8
<211> LENGTH: 58
<212> TYPE: RNA
<213> ORGANISM: Artificial Sequence
<220> FEATURE:
<223> OTHER INFORMATION: Synthetic Probe

<400> SEQUENCE: 8
gggacacaau ggauucguau ggguggsauc gggaagggcu acgaacaccg uaacggcc        58

<210> SEQ ID NO 9
<211> LENGTH: 60
<212> TYPE: RNA
<213> ORGANISM: Artificial Sequence
<220> FEATURE:
<223> OTHER INFORMATION: Synthetic Probe

<400> SEQUENCE: 9
gggacacaau ggauucguau ggguggsauc gggaagggcu acgaacaccg uaacggccga      60

<210> SEQ ID NO 10
<211> LENGTH: 64
<212> TYPE: RNA
<213> ORGANISM: Artificial Sequence
<220> FEATURE:
<223> OTHER INFORMATION: Synthetic Probe

<400> SEQUENCE: 10
gggacacaau ggauucguau ggguggsauc gggaagggcu acgaacaccg uaacggccga      60
caug                                                                   64

<210> SEQ ID NO 11
<211> LENGTH: 68
<212> TYPE: RNA
<213> ORGANISM: Artificial Sequence
<220> FEATURE:
<223> OTHER INFORMATION: Synthetic Probe

<400> SEQUENCE: 11
gggacacaau ggauucguau ggguggsauc gggaagggcu acgaacaccg uaacggccga      60
caugagag                                                               68
```

MULTI-APTAMER-BASED, CELL-SPECIFIC, ONE-STEP TUMOR CELL DETECTION ASSAYS

CROSS-REFERENCE TO RELATED APPLICATIONS

The present application is a continuation of PCT International Patent Application No. PCT/US2013/74797, filed Dec. 12, 2013, which claims priority to U.S. Provisional Patent Application No. 61/736,452, filed Dec. 12, 2012, and U.S. Provisional Patent Application No. 61/801,523, filed Mar. 15, 2013; the contents of each is specifically incorporated herein in its entirety by express reference thereto.

BACKGROUND OF THE INVENTION

Statement Regarding Federally Sponsored Research or Development

Not Applicable.

NAMES OF THE PARTIES TO A JOINT RESEARCH AGREEMENT

Not Applicable.

FIELD OF THE INVENTION

The present invention relates to the fields of clinical chemistry, oncology, and diagnostic medical assays. The invention provides multi-aptamer-based detection reagents, and corresponding diagnostic assays and methods for detection of target biomolecules. In exemplary embodiments, fluorescently-labeled detection reagents are provided for rapid, one-step detection of two or more distinct tumor biomarkers in a single biological sample, including, for example, the detection of multiple distinct biomarkers from a single drop of mammalian blood.

DESCRIPTION OF RELATED ART

Detection Methods for Circulating Tumor Cells

An ideal tumor cell detection assay should be 1) highly-specific; 2) sensitive enough to detect single tumor cells among millions of other cells; 3) lacking significant background signal; 4) accomplished in a one-step procedure; 5) performed using a minimal patient sample (e.g., a single drop of blood); 6) capable of high-throughput screening; and 7) low cost. To date, there are no such assays available. The is due to the fact that the reporting system of current probes used in cell detection assays are pre-labeled with the "active" fluorochrome, which is constantly signaling regardless of whether the probes are binding to tumor cells or not. The presence of the constant, "off-target" background signals limits the sensitivity of current assays, and the complex nature of the existing assay systems require tedious, multiple-step protocols to achieve sufficient results.

Currently, the CellSearch® technology (Veridex, LLC/Janssen Diagnostics, LLC, Raritan, N.J., USA) is the only FDA-approved platform for detection of circulating tumor cells in whole blood in specific cohorts of cancer patients. This semi-automated platform requires multiple steps including:

1) sample preparation: buffering blood, centrifuging, and loading on the CellPrep™ system (Veridex, LLC);

2) cell isolation: plasma/buffer removal, incubation with the Cell Immunomagnetic Enrichment Kit (Veridex, LLC, ferrofluids coated with antibodies), and magnetic separation of the cells of interest from blood cells;

3) cell staining: incubating enriched cells with fluorescent antibodies and nuclear staining reagent in a permeabilization buffer;

4) background removal: repeated magnetic separation of cells, removal of free antibodies and excess staining reagents by sequential washes; and 5) imaging: detecting labeled tumor cells (e.g., using a CellSpotter™ Analyzer; CellSearch, Veridex, LLC).

Although the final imaging and detection can be completed rapidly in this methodology, the multiple steps involved in sample preparation are both time- and labor-intensive. Moreover, the cost of this system and reagents presents a barrier to entry for many laboratories and clinical settings.

Similarly, several new assay systems have been reported in the literature that use different cell isolation/enrichment approaches, including the CytoTrack™ Assay (CytoTrack ApS; Lyngby, Denmark), which utilizes red blood cell lysis for cell isolation. However, all of these technologies use fluorescent antibodies for cell staining, and require multiple, labor-intensive steps to prepare and assay the sample. Importantly, none of the existing commercial methodologies represents a suitable platform for "point-of-care" screening, or facile, rapid sample analysis. Moreover, these systems are limited in their applicability to high-throughput platforms, multi-sample scale-up, and/or robotics-based analytical systems.

BRIEF SUMMARY OF THE INVENTION

The present invention overcomes these obstacles, as well as numerous additional limitations inherent in the prior art, by providing novel and non-obvious molecular biomarker detection assays that employ a cell-specific, intracellularly-activated, one-step detection system. This system, which is both highly sensitive and capable of detecting single tumor cells in populations of millions of normal cells, is highly accurate and reliable, and is facile in implementation and execution. Significantly, the assay system described herein can be accomplished rapidly—using a very small quantity of biological sample and a one-step, single-reagent protocol. In illustrative embodiments, the present assay system has been employed to rapidly and specifically detect single or multiple distinct biomarkers from different types of human tumor cells using only a single drop of the patient's blood as the specimen sample.

The present assay system provides a highly-desirable method for rapid tumor cell detection. Importantly, the disclosed assay may be readily performed as a one-step procedure—either in a traditional clinical laboratory environment, or even at the point-of-care, including remote, and distant locales outside the conventional clinical environs. In its simplest form, the disclosed assay system involves simply mixing a small volume of a biological sample (e.g., a single drop of a patient's blood will suffice) with a minimal number of reagents (in particular embodiments, a single reagent solution), incubating the test mixture briefly (in certain embodiments for as short a time as a few minutes), and then rapidly obtaining the results in a cost-effective, reproducible, and highly-sensitive manner. Particularly advantageous with the present invention, the results can be readily achieved, with little to no "off-target," "false-positive," or extraneous "background" signals. In particular commercially-relevant formats, the present assay can be scaled in a suitable form to permit adaptation for use in conventional, rapid, high-volume, high-throughput assay.

The assays of the present invention provide such desirable features, and affords a wholly-new approach to rapid, low-cost, screening of clinical samples, even at the point-of-care. FIG. 1A presents a schematic overview of the process. To achieve this goal, an assay system was developed that is both tumor cell-specific, and "active" (i.e., detectable) only within particular cells of interest that express the target molecule(s) for which the aptamer is specific (see, e.g., FIG. 1B). The new method is in sharp contrast to existing antibody-based assay systems found in the prior art (see e.g., FIG. 1C) that are constantly active, and consistently produce extraneous, off-target, and/or background signals.

In contrast to the existing technology, the novel assay system disclosed herein provides a unique "activatable" reporter system that includes: 1) a first aptamer probe sequence (e.g., an RNA or ssDNA oligonucleotide), which specifically targets a first biomarker of interest operably linked to a first reporter pair that includes a first donor moiety (i.e., a fluorescent label e.g., 6-FAM, Cy3, Cy5, Cy5.5, etc.) operably linked to a first acceptor moiety (quencher molecule), such that the first quencher molecule silences the first label in its native, or inactive, state.

In one embodiment, the invention provides compositions and methods for detecting one or more selected biomarker(s) of interest in a biological sample. In an overall and general sense, the method generally involves contacting a sample suspected of containing the selected biomarker(s) with a composition that comprises a reporter system that includes a first aptamer probe sequence that specifically targets (i.e., specifically binds to) a first biomarker of interest, wherein the aptamer is operably linked to a first reporter pair that includes a first donor moiety operably linked to a first acceptor moiety, such that the first acceptor moiety silences the first donor moiety in its native, or inactive, state, under conditions effective, and for a time sufficient, to detect the biomarker of interest in the sample.

Preferably the first half of the donor-acceptor pair (i.e., the donor moiety), will be operably linked to a detectable label, such as a fluorescent or biotinylated label. Exemplary labels include, but are not limited to, fluorescent labels such as 6-carboxyfluorescein (6-FAM), HEX, Texas Red®, Texas Red®-X, Rhodamine, Rox Reference Dye, Alexa Fluor® 488, Alexa Fluor® 584, Alexa Fluor® 633, Alexa Fluor® 660, Alexa Fluor® 680, R-phycoerythrin (R-PE), tetramethylrhodamine (TRITC), 5-carboxytetramethylrhodamine (5-TAMRA), a cyanine dye (including, without limitation, Cy2, Cy3, Cy3.5, Cy5, Cy5.5, or Cy7), IRDye® (800CW), or any combination thereof.

Preferably the second half of the donor-acceptor pair (i.e., the acceptor moiety), will be operably linked to a quencher molecule such as Dabcyl; a Black Hole Quencher® Dye such as BHQ-1, BHQ-2, or BHQ-3; one or more Cy5 NHS esters, such as Cy5Q or Cy7Q NHS ester; or an infrared non-fluorescent dark quencher dye, such as IRDye® QC-1, or any combination thereof.

In certain embodiments, the biomarker of interest will be specific for one or more particular cells or tissue types of interest. Preferably, the biological sample will contain one or more bodily fluids such as whole blood, serum, urine, CNS fluid, lymph, sputum, exudates, bronchial lavage, or any combination thereof. Preferably, the biological sample will be a blood sample obtained from a human, and in particular, a human patient.

In certain embodiments, the biomarker of interest will be specific for one or more particular mammalian tumor cells or cancer cells, such as breast cancer cells, lymphoma cells, leukemia cells, or other cancer cells. In an illustrative example herein, the biomarker of interest was a CD30+ antigen, whose presence in a sample was indicative of a circulating mammalian tumor cell within the assayed blood sample.

One of the unique features of the present invention is the ability to detect the selected biomarkers of interest rapidly, at room temperature, and from sample volumes that are quite small compared to those needed for conventional assays. In fact, the inventors have demonstrated that the sample volume may be between about 20 and about 250 µL, more preferably between about 30 and about 150 µL, and more preferably still, between about 50 and about 100 µL.

In the practice of the invention, the selected aptamer sequences are preferably comprised of RNA or ssDNA, and comprise, or consist essentially of, a nucleic acid sequence that is specific for (i.e., that specifically binds to) at least one tumor-specific biomarker. Such biomarkers may include, without limitation, nucleic acids such as dsDNA, ssDNA, dsRNA, and ssRNA, or a combination thereof As noted above, the selected aptamer sequence is preferably operably linked to a first detectable label. This may be accomplished by conventional biochemical linking techniques, including, without limitation, chemical conjugation, cross-linking, using one or more natural or synthetic linkers or linking agents, or any combination thereof.

Preferably the aptamer includes an oligonucleotide detector probe that is about 20, about 25, about 30, about 35, about 40, about 45, about 50, about 55, or about 60 or so nucleotides in length (although any suitable size sequence may be employed in the method as needed to effect a specific binding of the aptamer sequence to its target).

In particularly preferred embodiments, the aptamer will include an oligonucleotide probe that comprises, consists of, or alternatively, consists essentially of an RNA or ssDNA sequence that is about 30 to about 50 or so nucleotides in length. Exemplary oligonucleotide probes include those that comprise, consists essentially of, or alternatively, consist of, any one of the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

Optionally, when it is desirable to detect the presence of multiple biomarkers within a single sample, the reporter system may further include a second distinct aptamer probe operably linked to a second distinct reporter pair that includes a second donor moiety operably linked to a second acceptor moiety, such that the second acceptor moiety silences the second donor moiety in its native, or inactive, state, and further still, the reporter system may also further include a third distinct aptamer probe operably linked to a third distinct detectable label. In multi-detection embodiments, each aptamer will be selected for its particular specificity with a single target biomarker, and each aptamer will be operably linked to distinctly different labels, so that each may be identified and quantitated when multiple biomarkers are present in a given sample.

In the practice of the invention, the detectable label may be detected and/or quantitated by any conventional method known to those of ordinary skill in the art, such as, but not limited to, flow cytometry, immunophenotyping, tissue immunohistochemical stain, fluorescence microscopy, or a combination thereof One of the key advantages of the present method is the ability to assay the sample at ambient temperatures, and for relatively short incubation periods (as compared to conventional diagnostic assays). In certain examples, the inventors have shown that the method may be fully realized by contacting the sample with the labeled aptamer reporter system described herein for about 10 to about 60 minutes (and more preferably, for about 15 to about 40 minutes, or even about 20 to about 30 min or so), and preferably at ambient (i.e., "room") environmental temperature, although other assay temperatures (such as between about 0° C. and about 20° C.) may also be utilized in certain embodiments, as warranted.

In another embodiment, the invention provides compositions and methods for detecting a particular cell of interest, such as a circulating tumor cell, in a mammalian blood sample. Generally, the method includes the step of contacting the sample with a reporter system that comprises a first aptamer probe sequence that specifically targets a tumor-specific biomarker operably linked to a first reporter pair that includes a first donor moiety operably linked to a first acceptor moiety, such that the first acceptor moiety silences the first donor moiety in its native, or inactive, state, under conditions effective, and for a time sufficient, to detect the particular cell of interest, such as a circulating tumor cell, in the mammalian blood sample. In certain applications, the sample may consists essentially of a single drop of blood, and the particular cell of interest can be detected in the sample following incubation of the sample and the reporter system at room temperature for not more than about 20 to about 30 min. Advantageously, the present methods may also be readily adapted and configured for large-scale, multi-well microplate, and/or high-throughput sample analysis to facilitate rapid, low-cost, high-volume sample analysis, and reporting.

As described above, in a multi-aptamer iteration of the invention, the assay can optionally further include: 2) a second aptamer probe sequence that specifically targets a second biomarker of interest operably linked to a second reporter pair that includes a second donor moiety operably linked to a second acceptor moiety (quencher molecule), such that the second quencher molecule silences the second fluorescent label in its native, or inactive, state.

And, in such multi-aptamer applications, where the simultaneously detection of three different biomarkers in a single sample is desired, the assay can further optionally include: 3) a third aptamer probe sequence that specifically targets a third biomarker of interest operably linked to a third reporter pair that includes a third donor moiety (fluorescent label) operably linked to a third acceptor moiety (quencher molecule), such that the third quencher molecule silences the third fluorescent label in its native, or inactive, state.

Where the detection of four biomarkers of interest is desired, the assay system may further optionally include: 4) a fourth aptamer probe sequence that specifically targets a fourth biomarker of interest operably linked to a fourth reporter pair that includes a fourth donor moiety (fluorescent label) operably linked to a fourth acceptor moiety (quencher molecule), such that the fourth quencher molecule silences the fourth fluorescent label in its native, or inactive, state.

The improved methods disclosed herein permit a facile procedure that provides for the rapid, and highly-sensitive, detection of one or more selected target molecules, without producing any "off-target" non-specific labeling, false-positive results, or extraneous background signals. Although the new assay system can be quickly performed in a single-tube, one-step protocol, it is also particularly well suited for employment in multi-well, multi-sample analyses, including, for example, high-throughput screening methodologies, and robotics platform-based analytical systems. Moreover, the new, single-step assay facilitates sample analysis and high throughput screening capabilities at a much-reduced cost compared to conventional diagnostic systems currently in use for detection of cancer cells in vivo or in vitro.

Aptamer Probes

Aptamers are single-stranded DNA or RNA molecules isolated and obtained from oligomers that bind to a specific chemical or biological molecule with high affinity and selectivity. They have been used for detection of biomolecules. Since the aptamers are based on oligonucleotides, they have many advantages over protein-based antibodies. That is to say, they can be obtained ex vivo and a variety of organic and inorganic substances may be used as target molecules. In addition, once a specific aptamer binding specifically to a specific target molecule is identified, it can be produced in large scale at low cost.

The aptamers of the present invention are preferably RNA or ssDNA, and typically about 25 or 30 to about 50 or 60 or so nucleobases in length. Preferably, they specifically bind to one or more targets including cells, proteins, viruses, drugs, etc. and preferably exhibit high-affinity binding to their specific targets. Because the aptamer probes of the present invention are small oligonucleotides, they have little to no immunogenicity in vivo, exhibit a high efficiency of tissue penetration, and do not stain the background in necrotic tumor tissues.

Notably, in contrast to the currently used probes, the aptamer probes described herein do not constantly emit fluorescent signals (e.g., is "inactive") because the fluorochrome is completely blocked by the corresponding quencher molecule present in the same aptamer probe. However, when tumor cells are contacted with the aptamer probe, it is internalized by the cell, and subsequently degraded within target cells, such as lymphoma tumor cells. As a result, the paired fluorochrome and quencher are then separated, which "activate" the fluorescent reporter, resulting in signal emission exclusively within the tumor cells, and no extraneous or background signal from non-tumor cells. The absence of off-target signals makes this assay system much more sensitive (and specific) for tumor cell detection than any of the currently used commercial assay systems.

Reporter Systems for the Aptamer Probes

Fluorochromes having emission wavelengths from 450 to 800 nm can be conveniently employed as fluorescent donor moieties for use in constructing the aptamer-based detection reagents disclosed herein.

For the acceptor moieties, several well-known quencher molecules are also useful in the practice of the invention (including, without limitation, Dabcyl (Exiqon, Inc.), one or more Black Hole Quencher® Dyes [e.g., BHQ-1, BHQ-2, and BHQ-3 from Biosearch Technologies, Inc., Novato, Calif., USA], one or more Cy5 NHS esters [e.g., Cy5Q or Cy7Q NHS esters from GE Healthcare Life Sciences, Piscataway, N.J., USA], and one or more IRDyes® [e.g., QC-1 [Infrared non-fluorescent dark quencher from LI-COR Biosciences, Lincoln, Nebr., USA], or any combination thereof.

The selected aptamer oligonucleotide sequences may be prepared by any suitable method known to those of ordinary skill in the art, including, for example using oligonucleotide synthesis. The aptamers of the present invention may be conjugated with one or more different fluorochrome-quencher pairs at the 5'- and/or 3'-ends using one or more conventional chemical linkers or conjugation methodologies known to those of ordinary skill in the art.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

Figure 2:
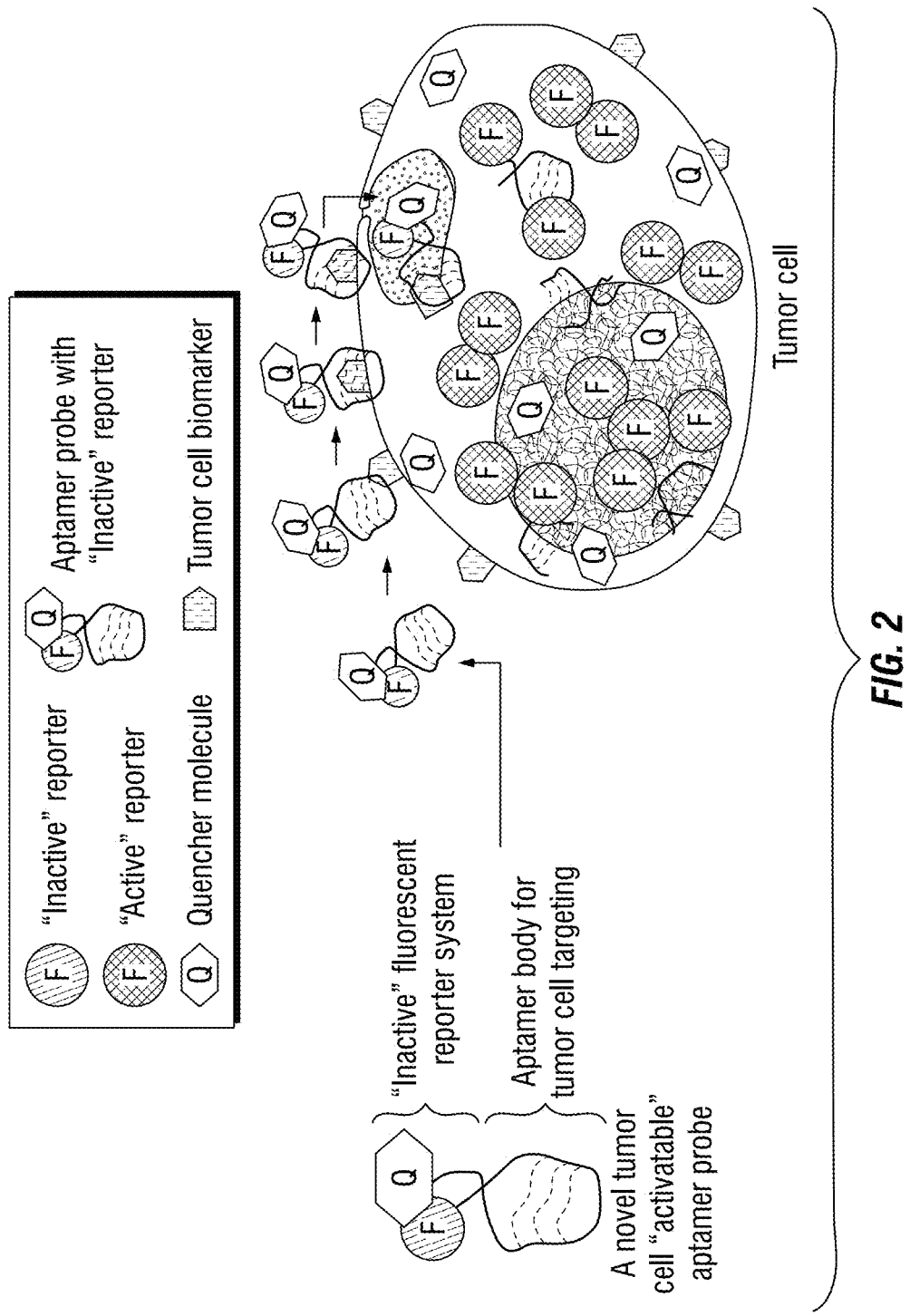

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

Figure 3:
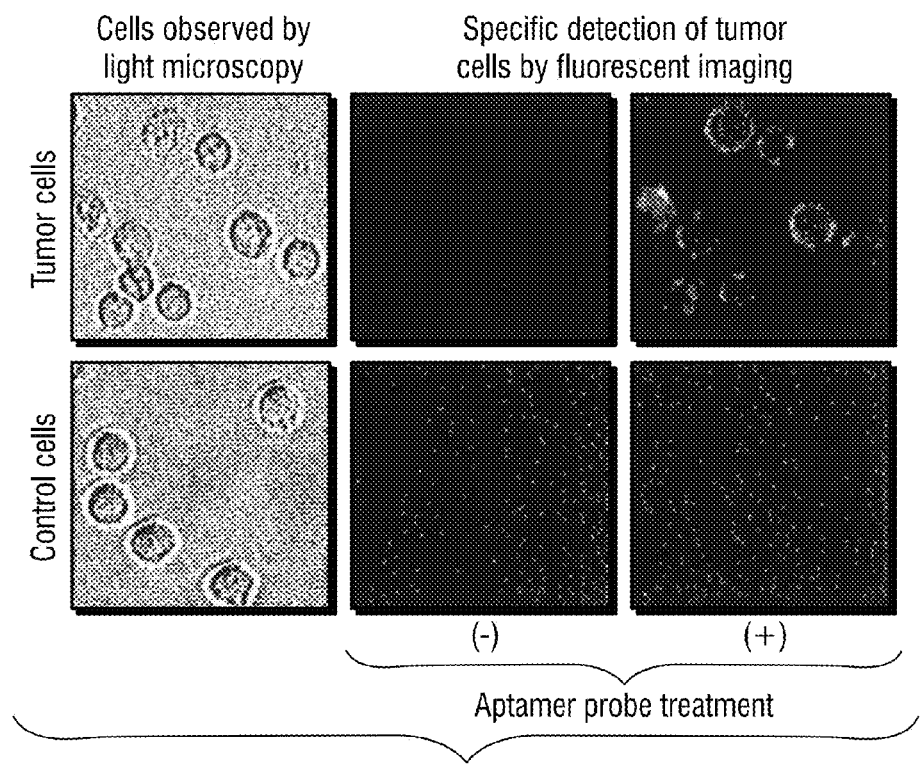
Figure 4A:
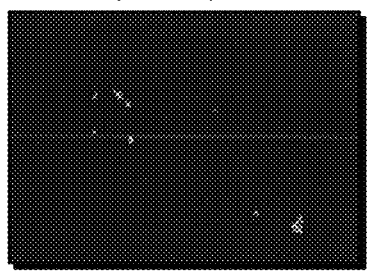
Figure 4B:
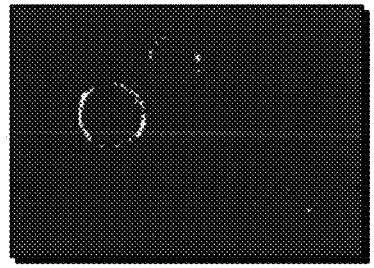
Figure 4C:
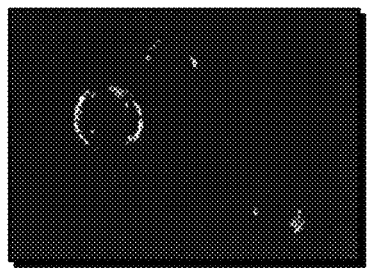
Figure 4D:
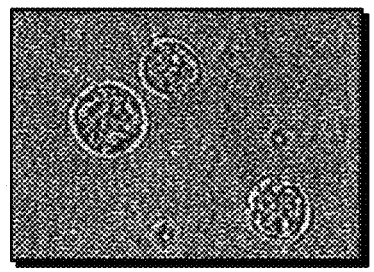
Figure 5A:
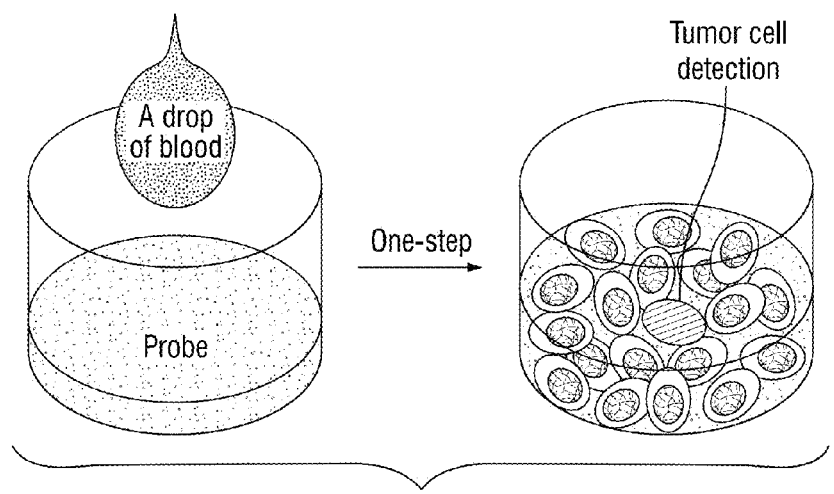
Figure 5B:
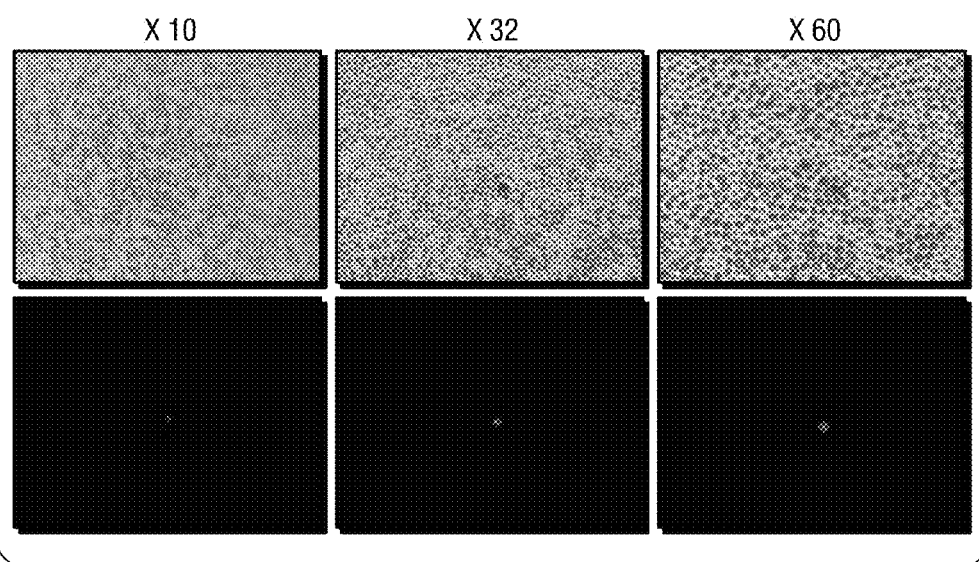
Figure 6A:
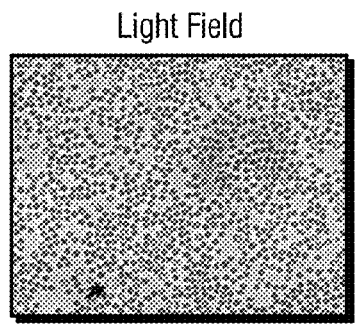
Figure 6C:
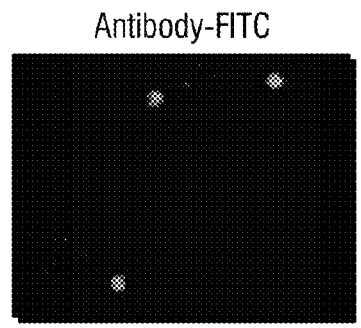
Figure 6B:
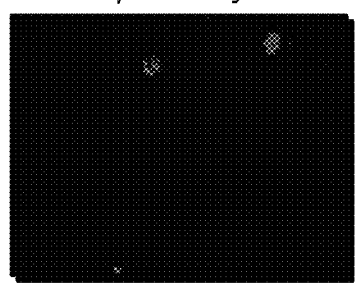
Figure 6D:
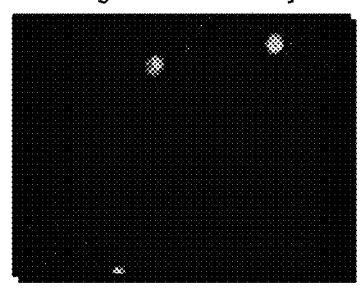
Figure 7A:
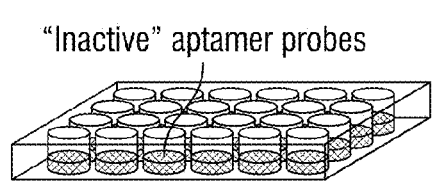
Figure 7B:
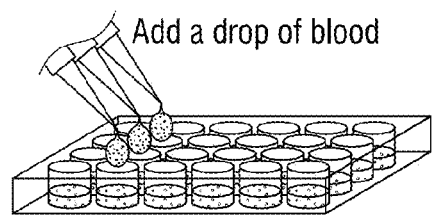
Figure 7C:
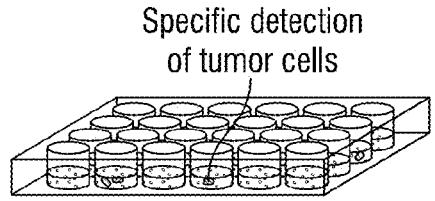
Figure 8:
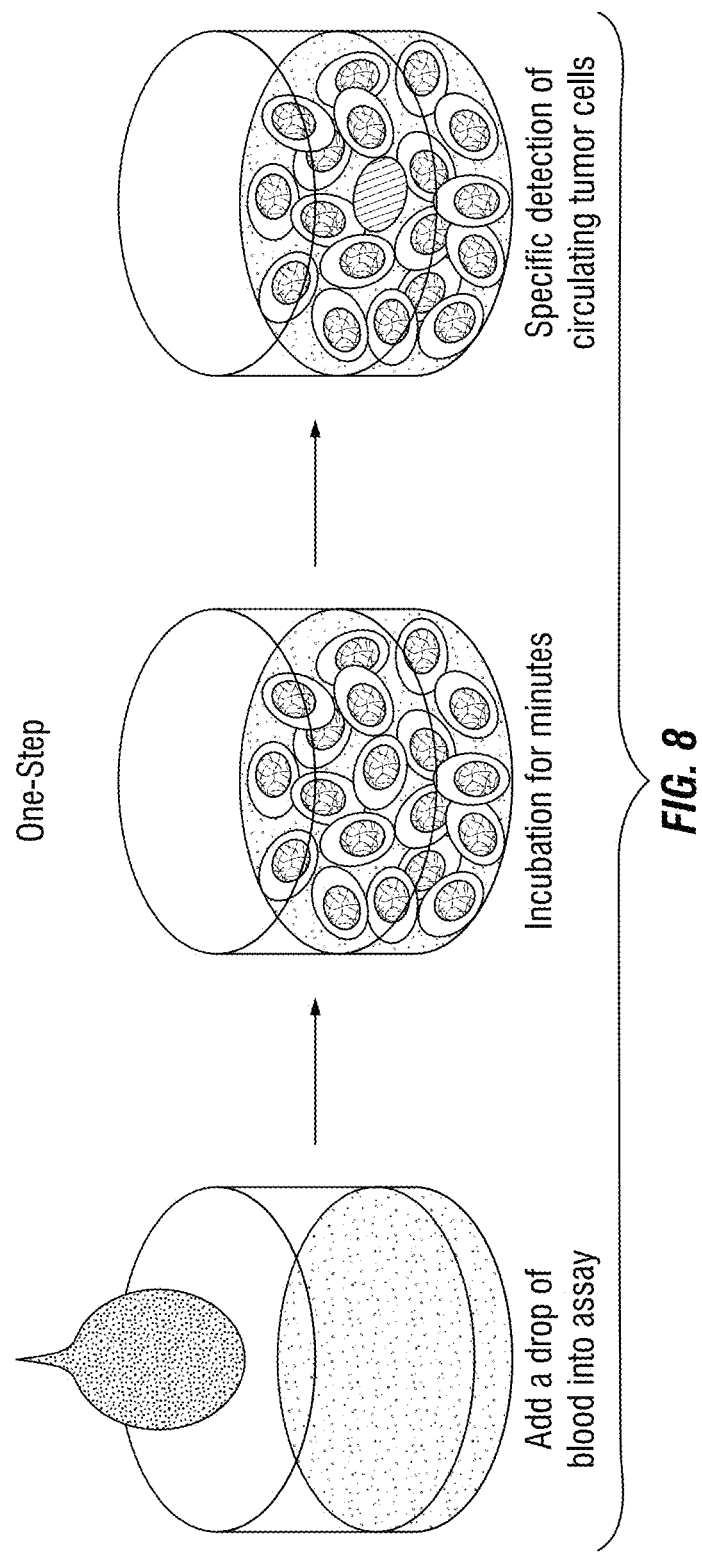
Figure 9:
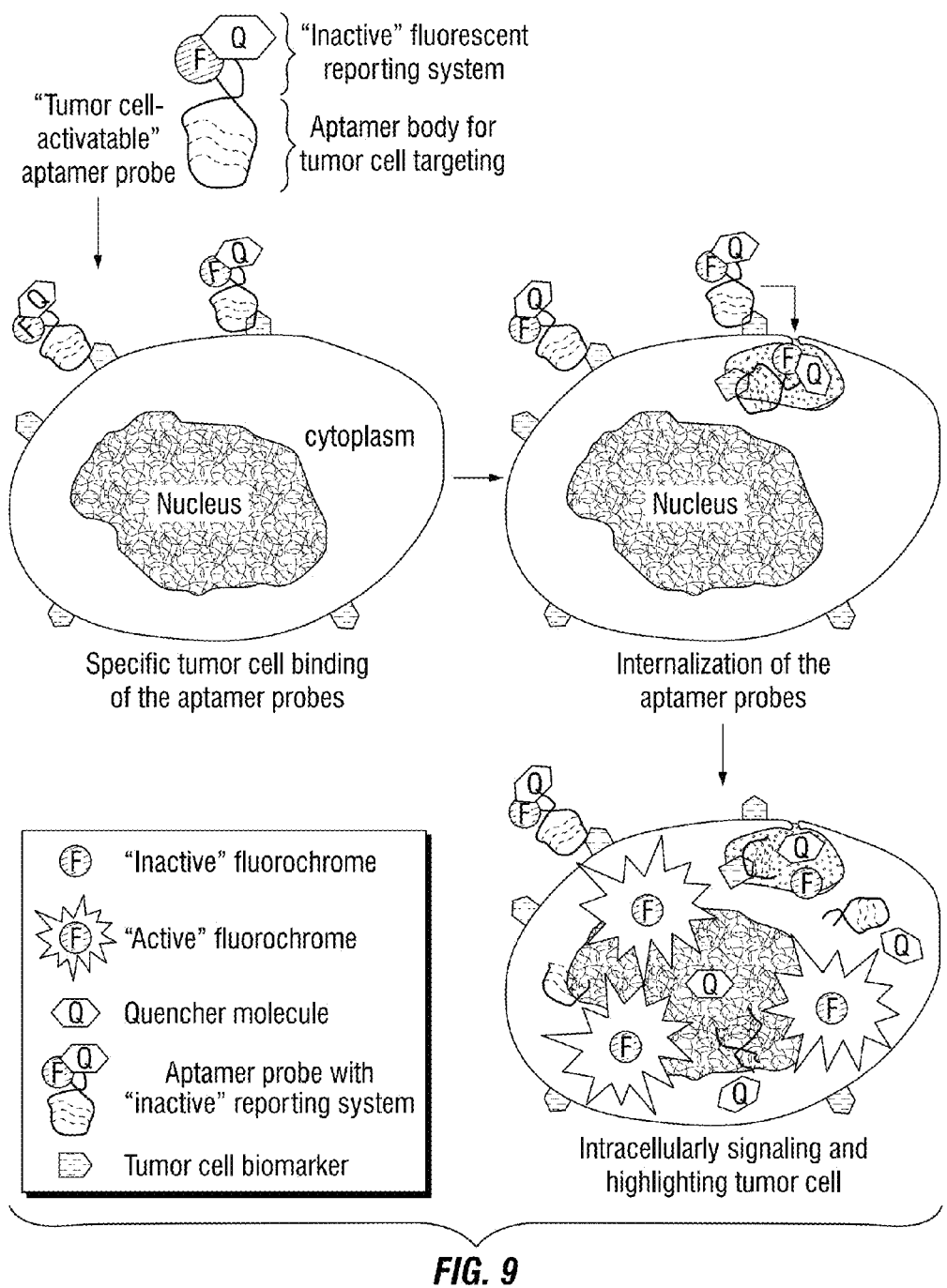
Figure 10:
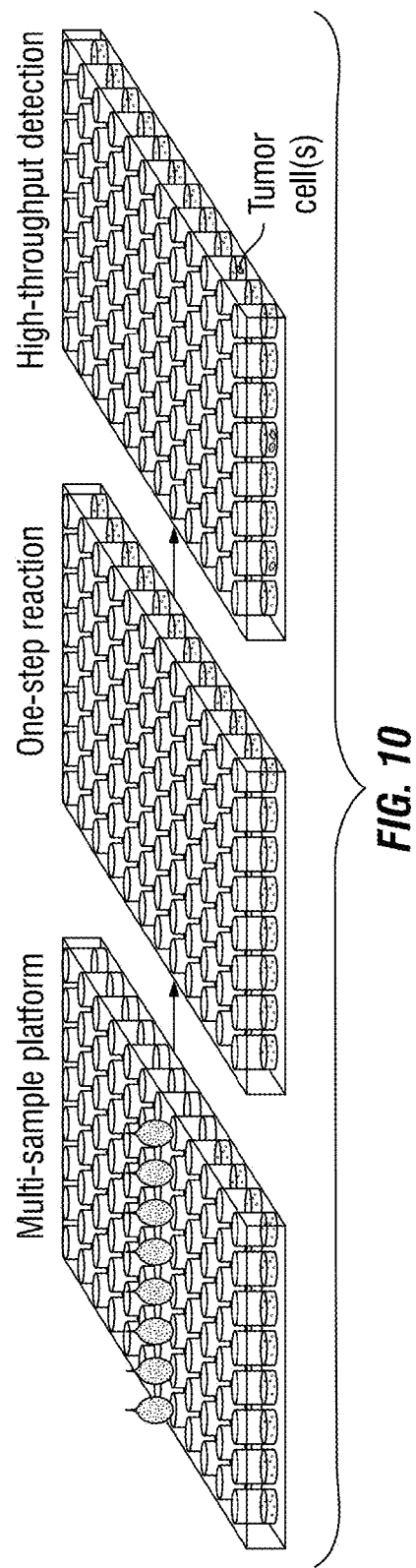
Figure 11:
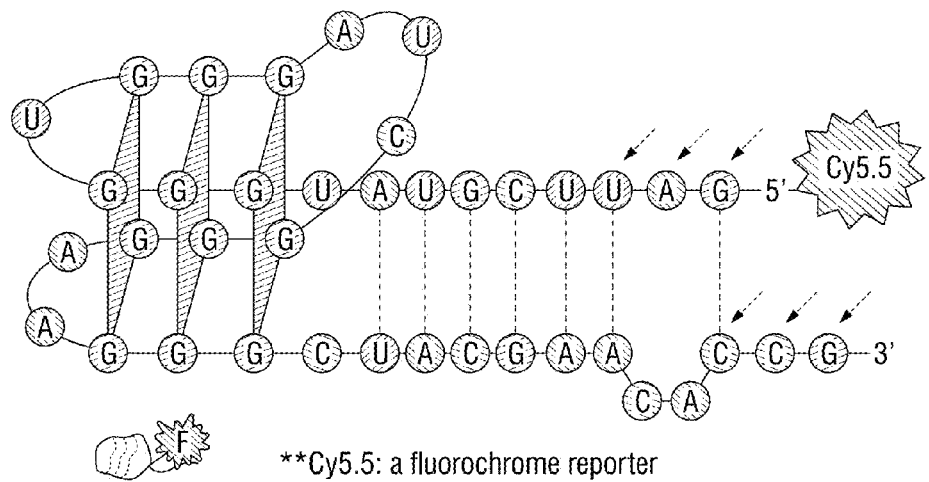

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1A illustrates an "ideal" assay for rapid tumor detection in a drop of blood; FIG. 1B illustrates an assay that employs a "tumor cell-activated" probe which exclusively highlights tumor cells with no off-target signals; and FIG. 1C shows a standard prior art assay that uses constantly "active" probes which can highlight tumor cells and also show off-target signals;

FIG. 2 shows an illustrative assay of the present invention which is specifically "activated" and emits signals exclusively within tumor cells. The designed probes have an aptamer body that specifically targets biomarkers of tumor cells, and carries an "activatable" reporter system (a pair of fluorochrome and quencher molecules). Under normal conditions, the quencher molecule blocks fluorochrome on the same aptamer and renders it "inactive." Specifically binding to tumor cells will lead to intracellular internalization and subsequent endosomal degradation of the aptamer probes. Releasing and separation of fluorochrome from the quencher molecule results in "active" imaging signals exclusively within tumor cells. Thus, this assay highlights only tumor cells with no off-target background signals;

FIG. 3 shows cultured lymphoma tumor cells and control lymphoma cells were incubated with or without the aptamer probes. The aptamer probes were activated exclusively within tumor cells and thus, specifically highlighted CD30+ lymphoma tumor cells with no background signals (upper row). In contrast, no off-target signals were detected in control lymphoma cells that do not express CD30 biomarker (lower row);

FIG. 4A, FIG. 4B, FIG. 4C, and FIG. 4D show intracellular activation and illuminating aptamer probes; the merged image is shown in FIG. 4D;

FIG. 5A and FIG. 5B show an overview of the one-step assay: simply added a drop of patient's blood into assay system for tumor cell detection. FIG. 5B shows the detection of lymphoma tumor cells. After 20 min's incubation, specimens were examined by fluorescent microscope (lower row). Single CD30+ lymphoma cell (arrow) was detected among a million of normal blood cells. Upper row is light microscopy of blood cells;

FIG. 6A, FIG. 6B, FIG. 6C, and FIG. 6D show double staining of lymphoma tumor cells: FIG. 6A shows light-field microscopy; FIG. 6B shows Aptamer-Cy3 label; FIG. 6C shows antibody-FITC labeled; and FIG. 6D shows the merged image which confirmed that the aptamer probes (in red) specifically detected CD30+ lymphoma tumor cells as well as antibody staining (in green);

FIG. 7A, FIG. 7B, and FIG. 7C show an illustrative robotic protocol featuring the one-step, high-throughput, highly sensitive and specific assay kit for early detection of circulating tumor cells in a single drop of blood specimens;

FIG. 8 shows a schematic illustration of the one-step assay system of the present invention useful in detecting, inter alia, circulating tumor cells;

FIG. 9 illustrates shows a one-step, tumor cell-activatable, intracellular signalizing assay system for detection of circulating tumor cells in accordance with one aspect of the present invention;

FIG. 10 shows an illustrative use of the new assay system in the creation of a high throughput, multi-sample microtiter plate based method suitable for robotic assay applications;

FIG. 11 shows an illustrative synthetic RNA-based CD30 aptamer probe useful in the practice of the present invention having the sequence:

```
                                          (SEQ ID NO: 1)
5'-gauUCGUAUGGGUGGGAUCGGGAAGGGCUA
CGAACAccg-3'.
```

Figure 12:
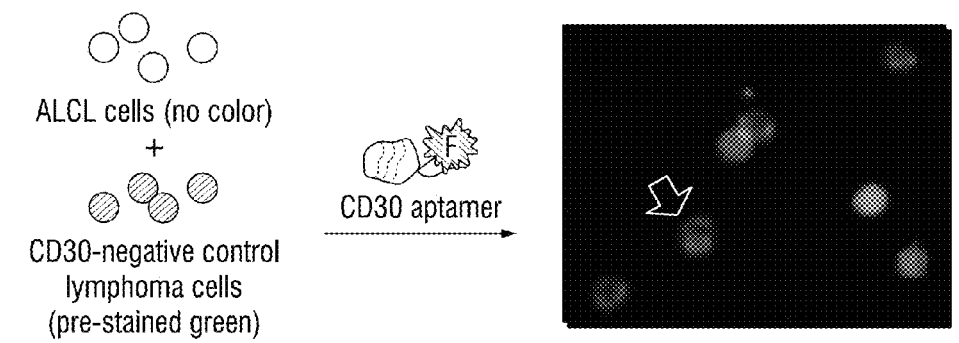
Figure 13A:
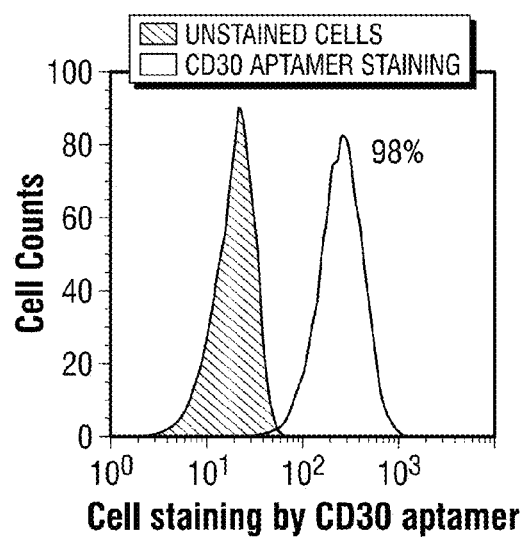
Figure 13B:
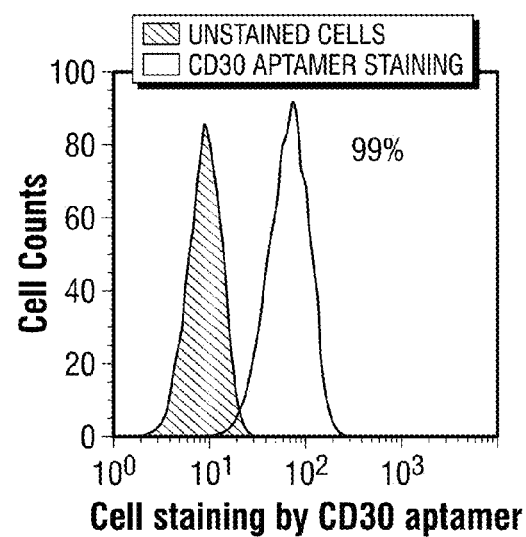
Figure 13C:
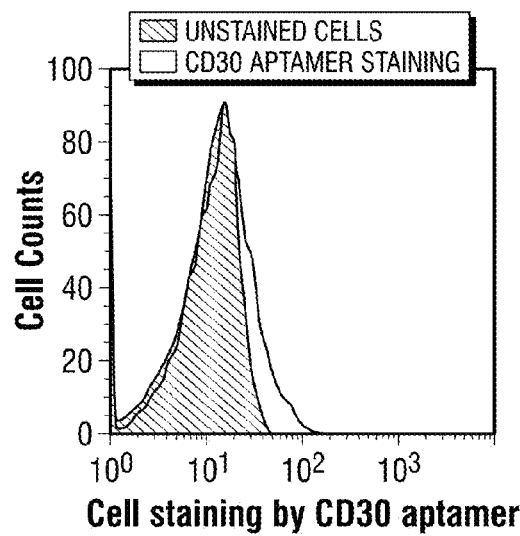
Figure 13D:
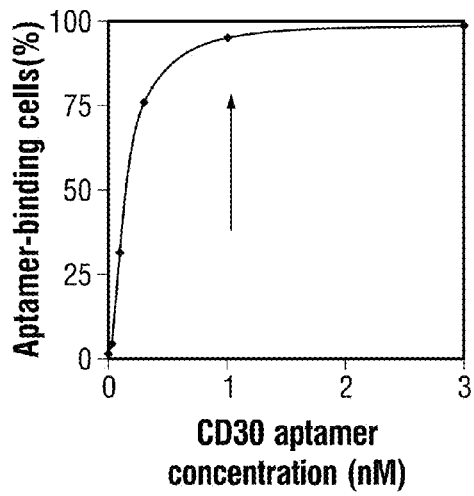
Figure 13E:
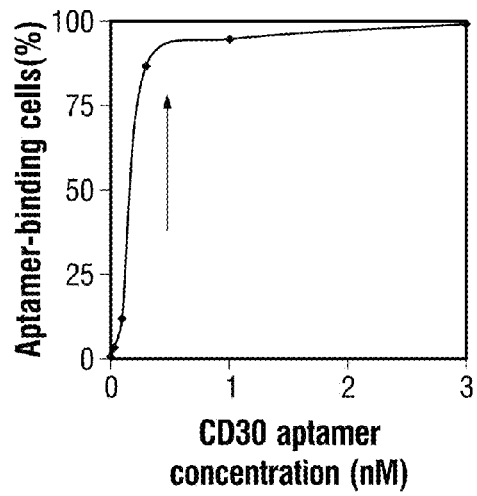
Figure 13F:
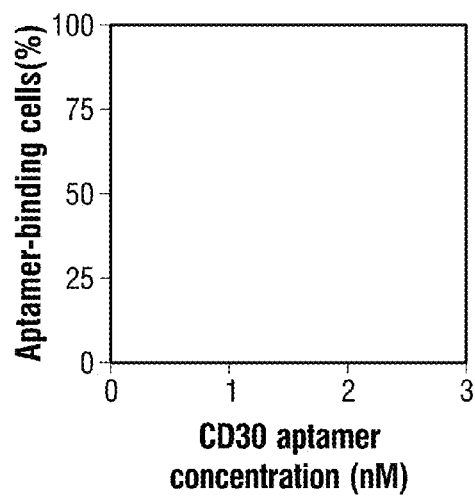
Figure 14A:
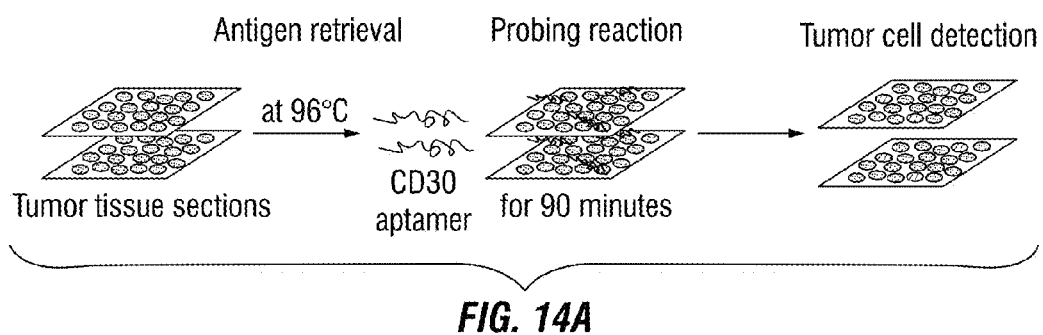
Figure 14B:
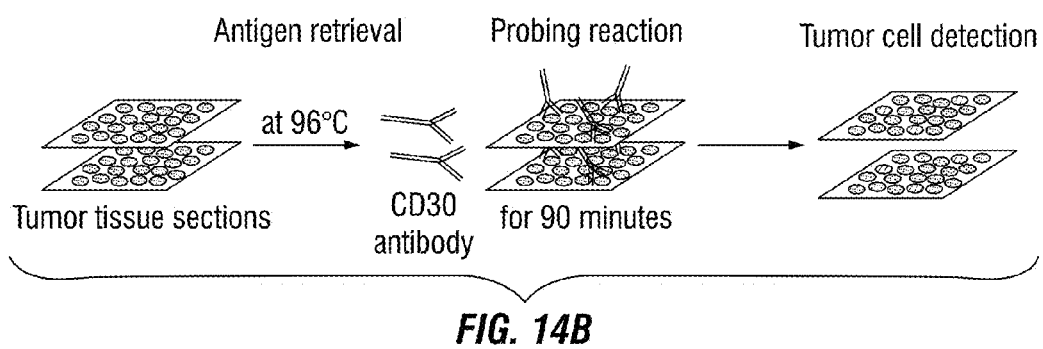
Figure 15A:
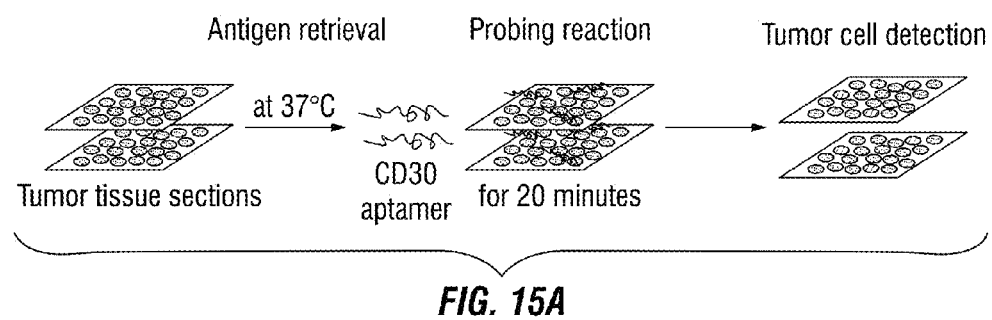
Figure 15B:
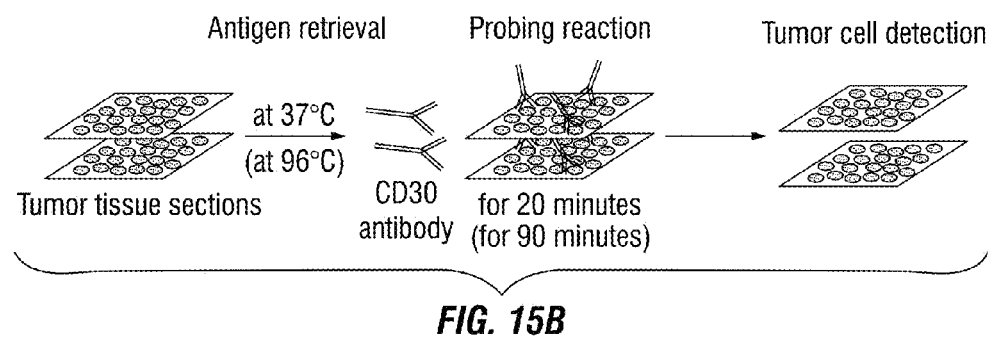
Figure 16:
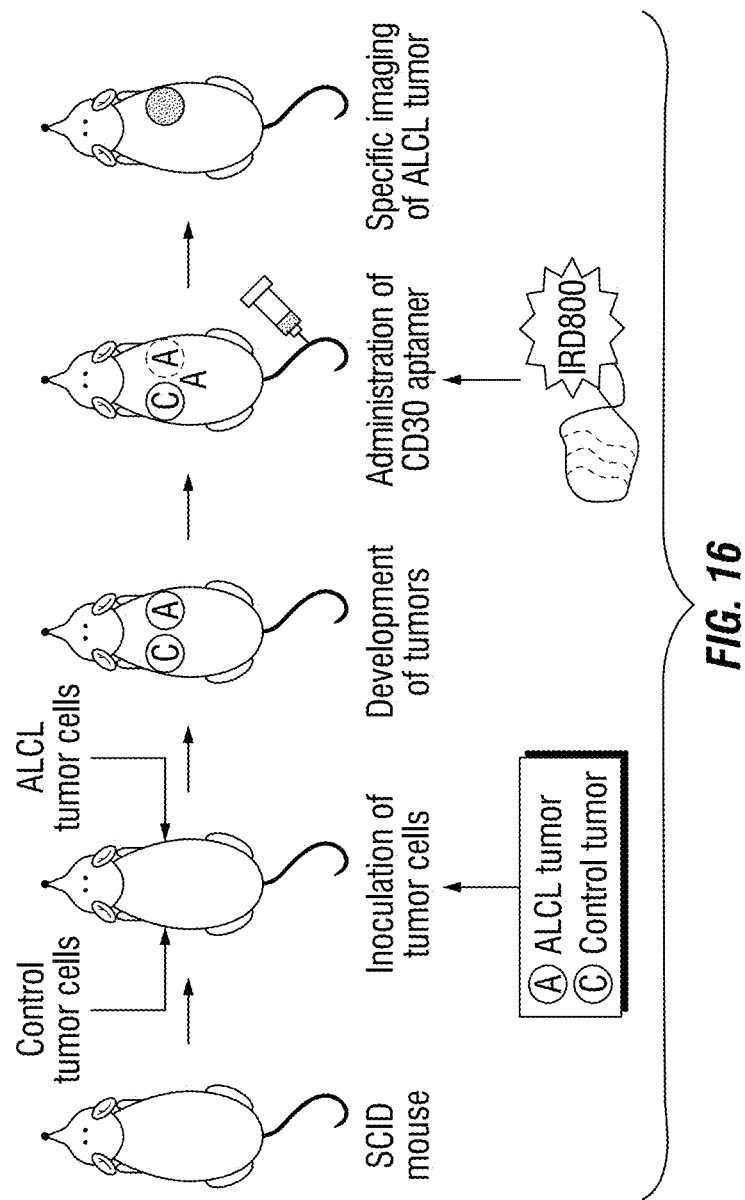
Figure 17:
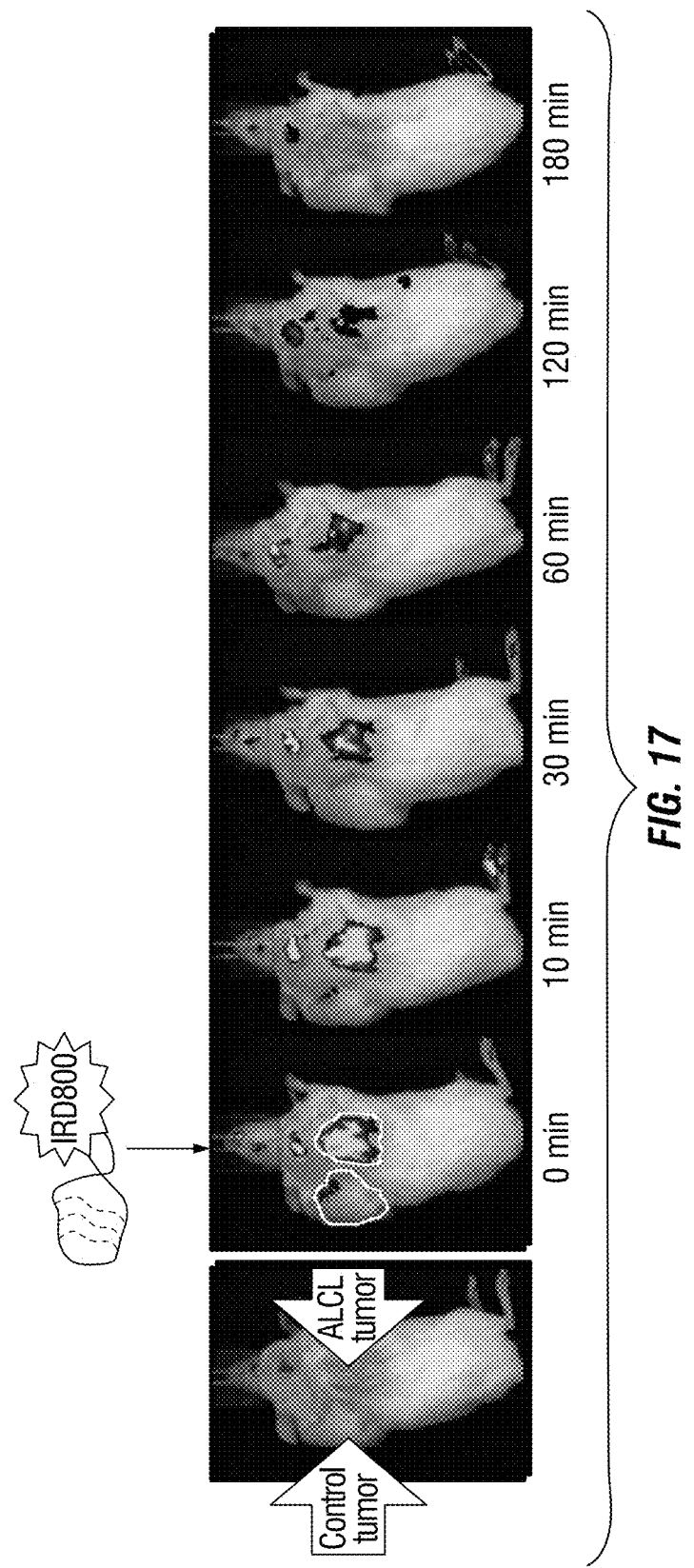
Figure 18:
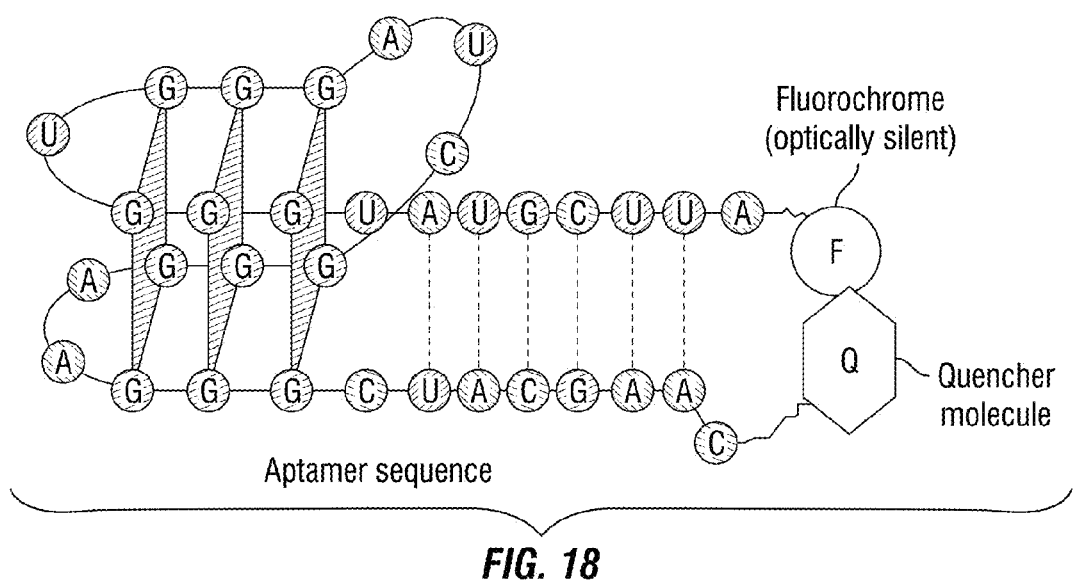
Figure 19A:
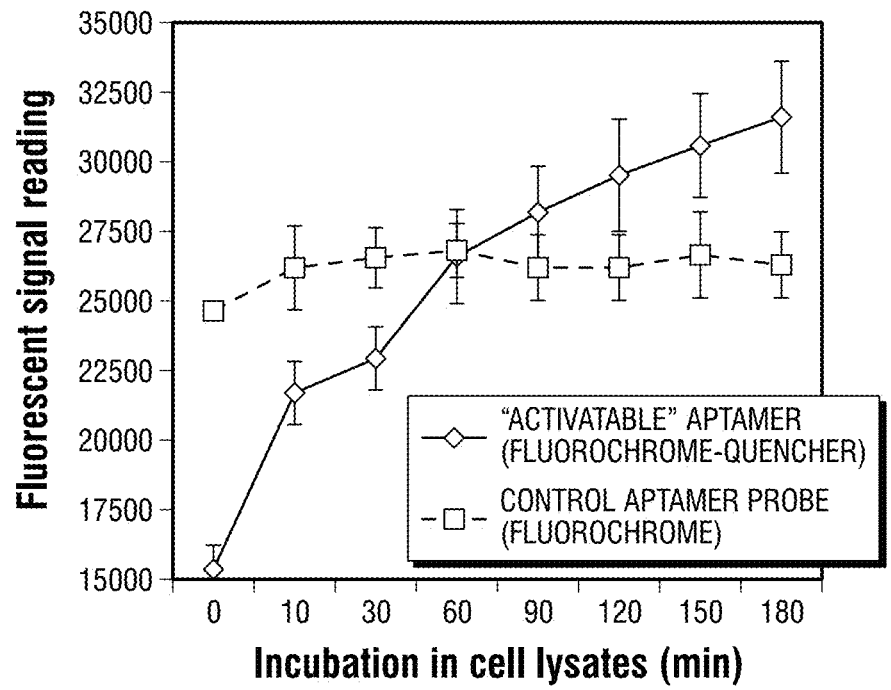
Figure 19B:
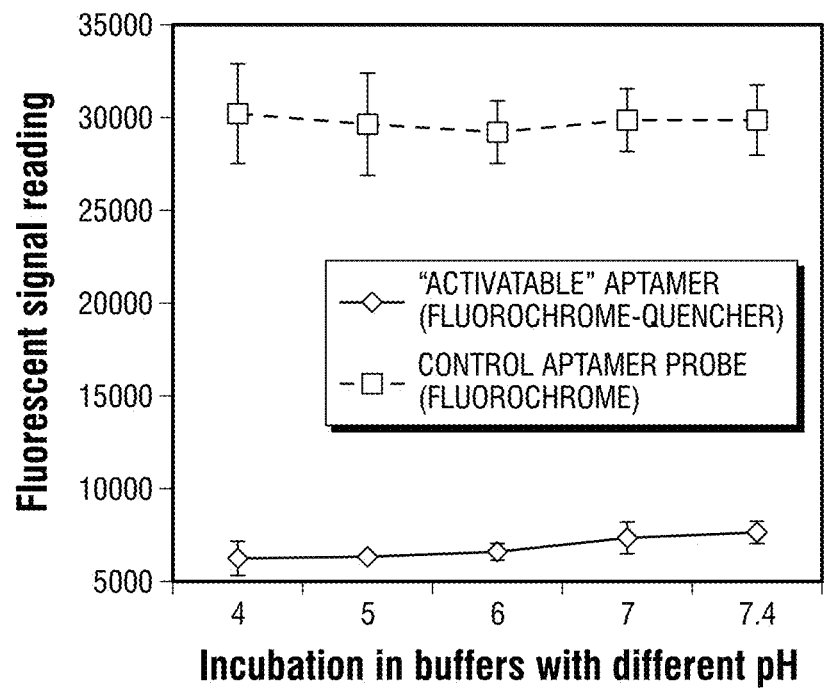
Figure 23:
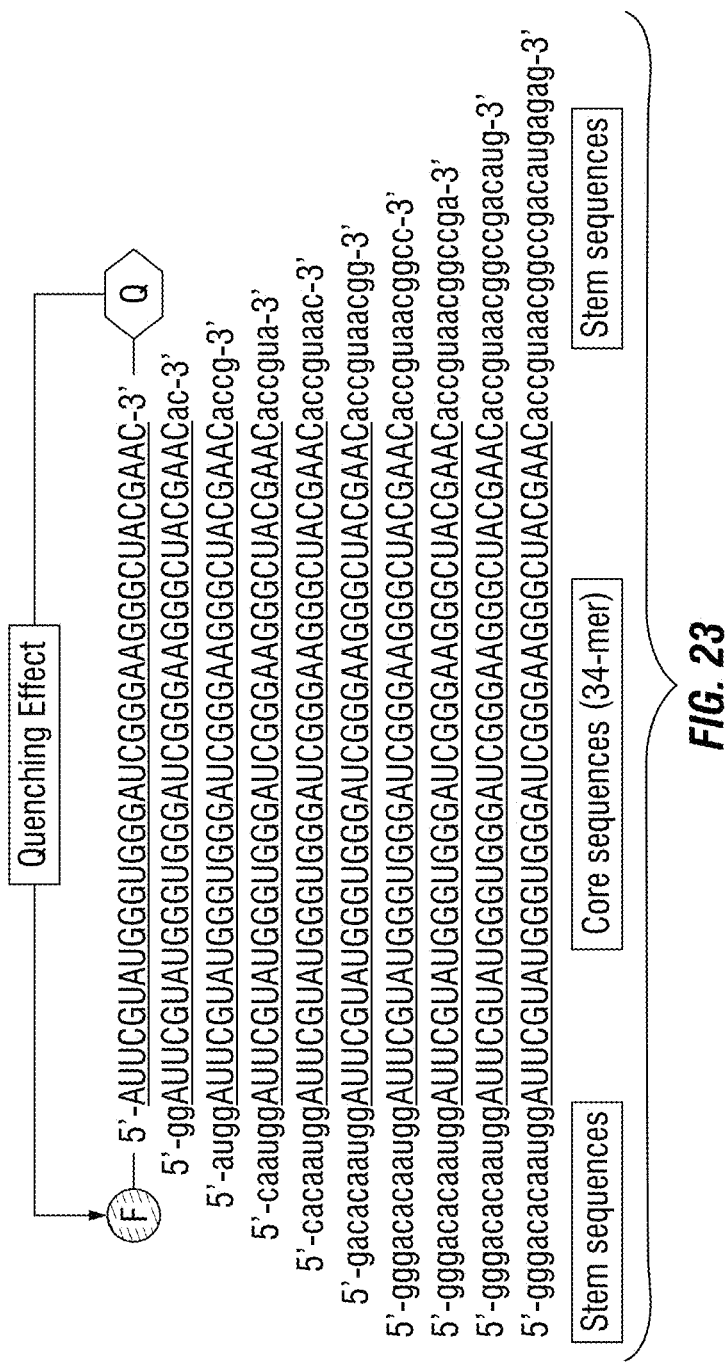
Figure 24A:
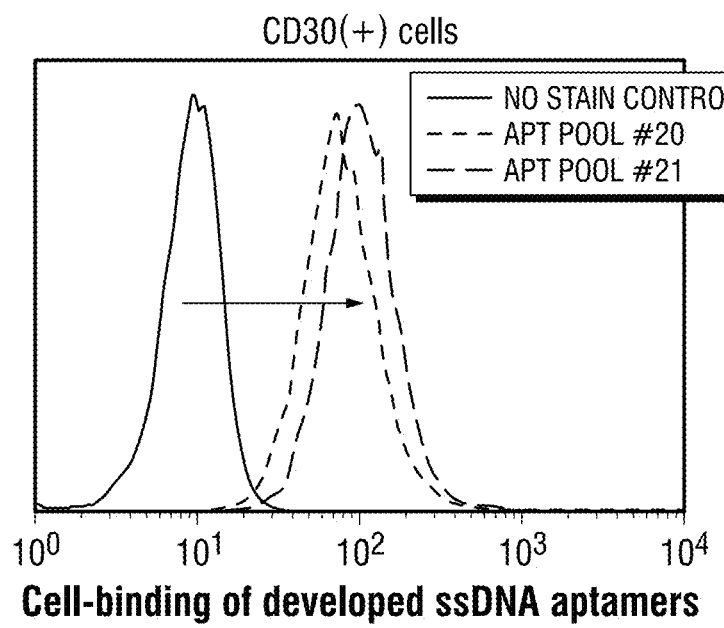
Figure 24B:
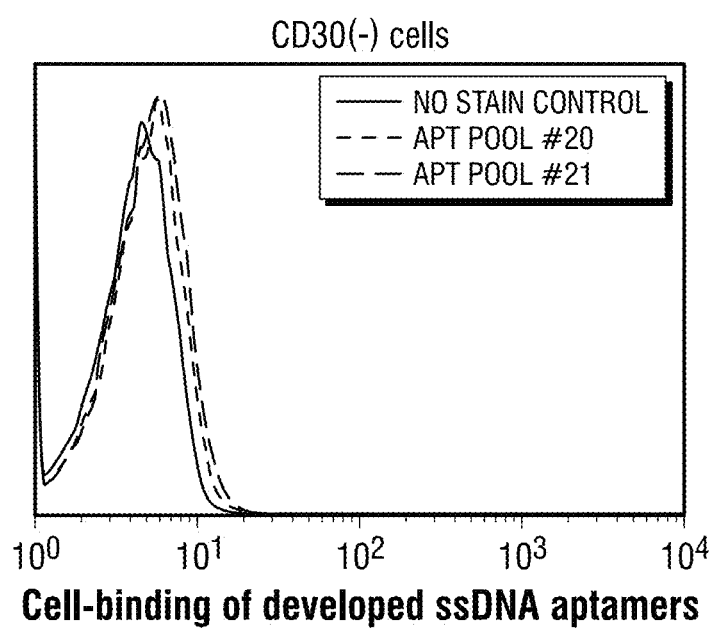
Figure 25:
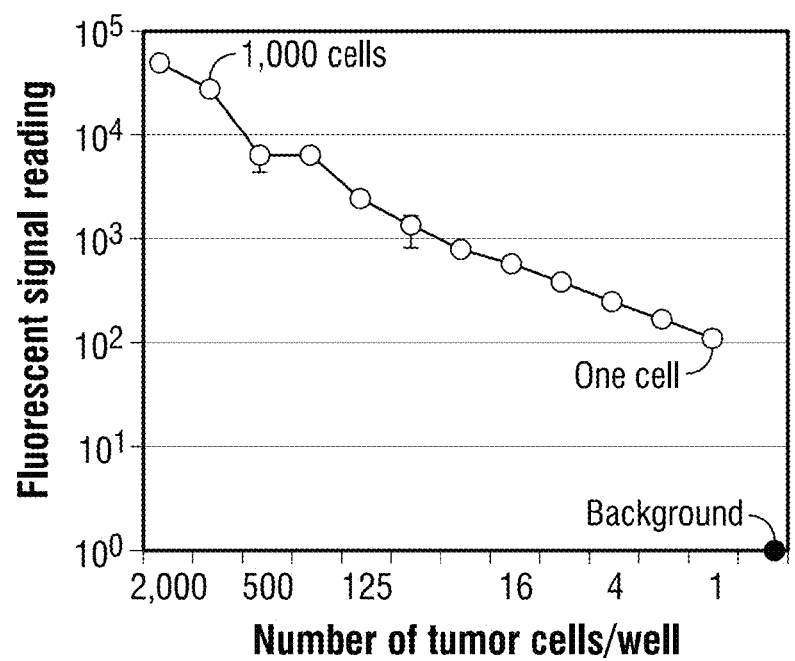
Figure 26:
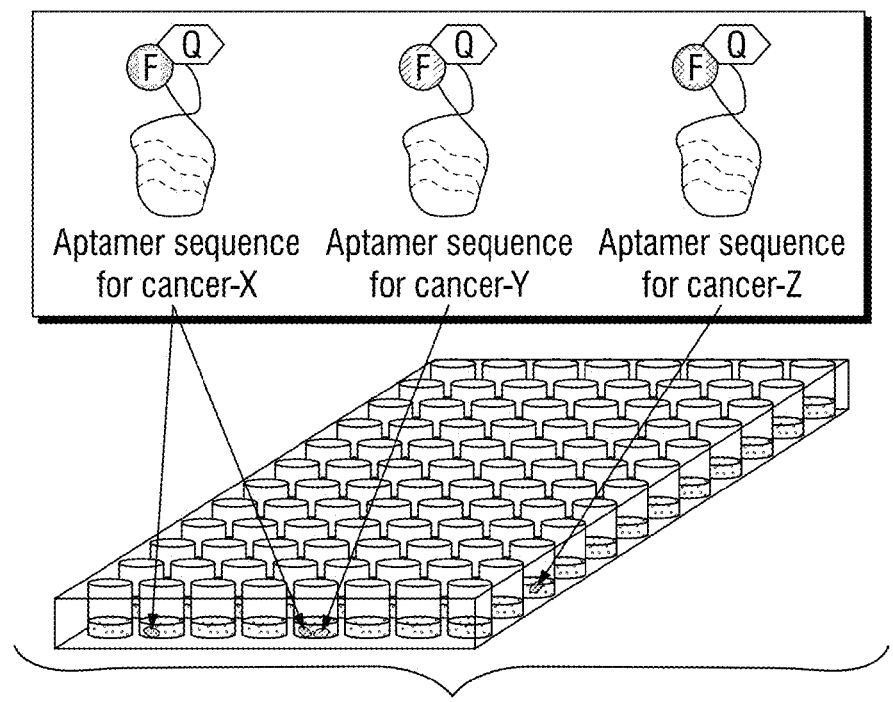

For tracking purposes, the aptamer was conjugated with fluorochrome Cy5.5 in accordance with one aspect of the present invention;

FIG. 12 shows specific staining of intact ALCL cells by the CD30 aptamer of FIG. 14A and FIG. 14B;

FIG. 13A, FIG. 13B, FIG. 13C, FIG. 13D, FIG. 13E, and FIG. 13F illustrate the high affinity of aptamer probe to lymphoma cells that express CD30 biomarker in accordance with one aspect of the present invention;

FIG. 14A and FIG. 14B show specific staining of lymphoma tissues by a synthetic CD30 aptamer probe in accordance with one aspect of the present invention;

FIG. 15A and FIG. 15B show an illustrative modification of conventional tissue immunostaining using a synthetic CD30-specific aptamer probe in accordance with one aspect of the present invention;

FIG. 16 demonstrates a schematic of the protocol for specific imaging of xenografted lymphoma tumor by aptamer probe;

FIG. 17 demonstrates results of the specific imaging of xenografted lymphoma tumor by aptamer probe in a rodent animal model;

FIG. 18 illustrates a unique aptamer probe (nucleotides 2 to 35 of SEQ ID NO:1) in accordance with one aspect of the present invention. It has a sequence for specific tumor cell targeting and an "intra-tumor cell activatable" reporter system composed of a pair of fluorochrome-quencher molecules. In the absence of tumor cells the fluorochrome is optically silenced ("inactive") by the paired quencher molecule;

FIG. 19A and FIG. 19B show optical activation of the aptamer probes in tumor cell lysates (FIG. 19A), but not affected by low pH conditions (FIG. 19B). In contrast, the control aptamer containing the same fluorochrome alone and no quencher molecule was signaling consistently;

FIG. 20A and FIG. 20B show tissue diagnosis of anaplastic large T-cell lymphoma tumor. FIG. 20A shows the characteristic morphology of lymphoma tumor cells; FIG. 20B shows the CD30 expression of tumor cells confirmed by immunohistochemical stain with antibody;

FIG. 21 shows an illustrative "intra-tumor cell activatable" aptamer probe. The reporter system is optically silent in the absence of tumor cells; Aptamer sequence contains the tumor cell-binding core sequence and stem sequence, length of which is correlated quenching effect of reporter fluorochrome;

FIG. 22 shows examples of reporter systems with different pairs of fluorochrome-quencher molecules that may be used in the ODOSA methods disclosed herein;

FIG. 23 shows examples of optimizing aptamer sequences (here, a series of 34-mer to 72-mer is shown; SEQ ID NO:2 to SEQ ID NO:11, respectively) to facilitate the highest binding affinity/specificity for CD30-expressing tumor cells with the lowest background signal;

FIG. 24A and FIG. 24B illustrate specific binding of exemplary ssDNA aptamers specific for CD30-expressing cells (FIG. 24A), but not to control cells (FIG. 24B);

FIG. 25 shows recorded fluorescent signals in a digital format by BioTek microplate reader;

FIG. 26 shows an exemplary ODOSA platform for simultaneous detection of different circulating tumor cells in a single blood sample.

Figure 27A:
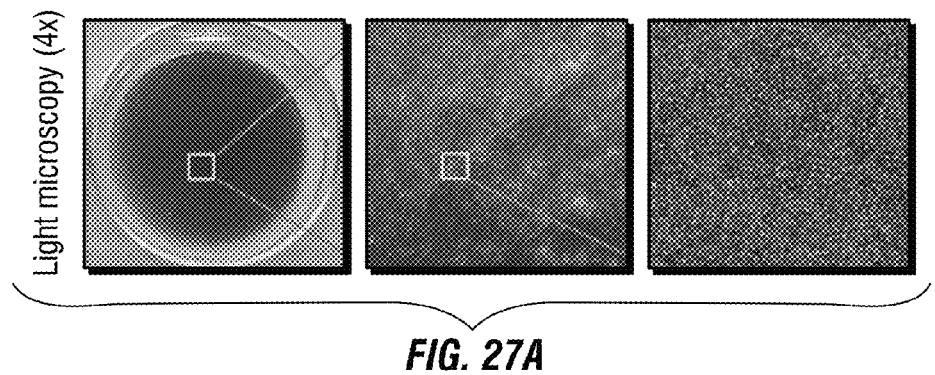
Figure 27B:
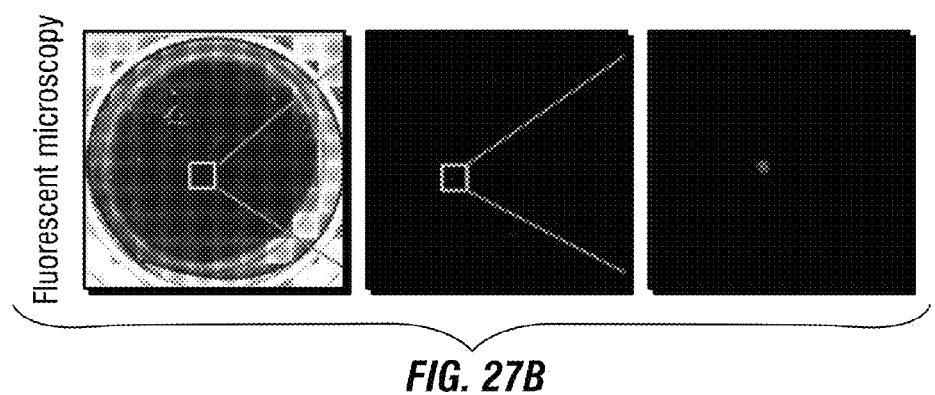
Figure 28A:
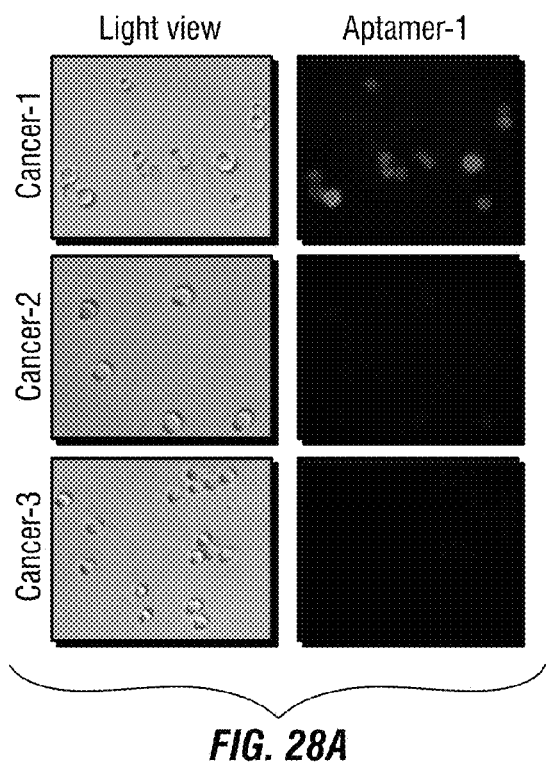
Figure 28B:
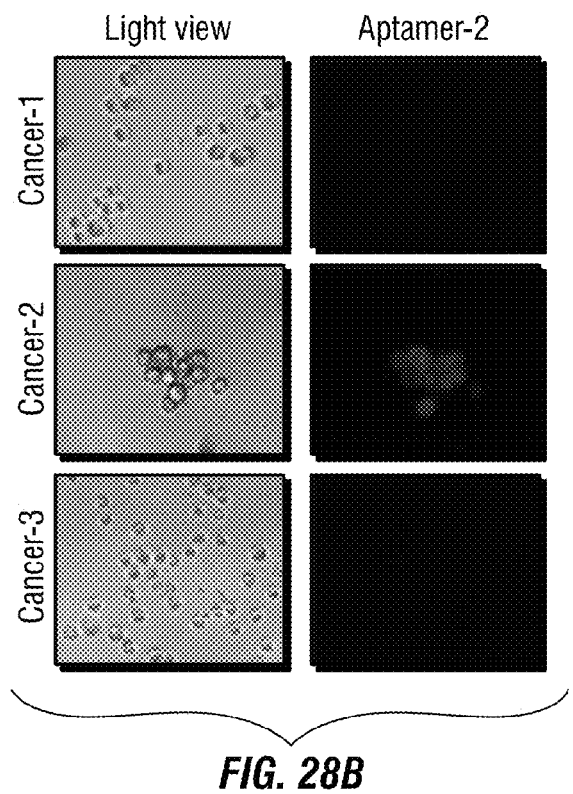
Figure 28C:
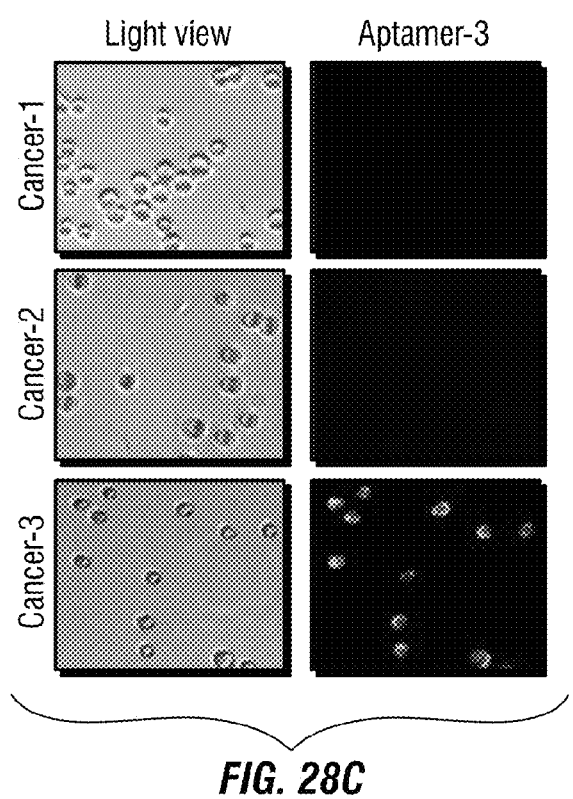
Figure 29A:
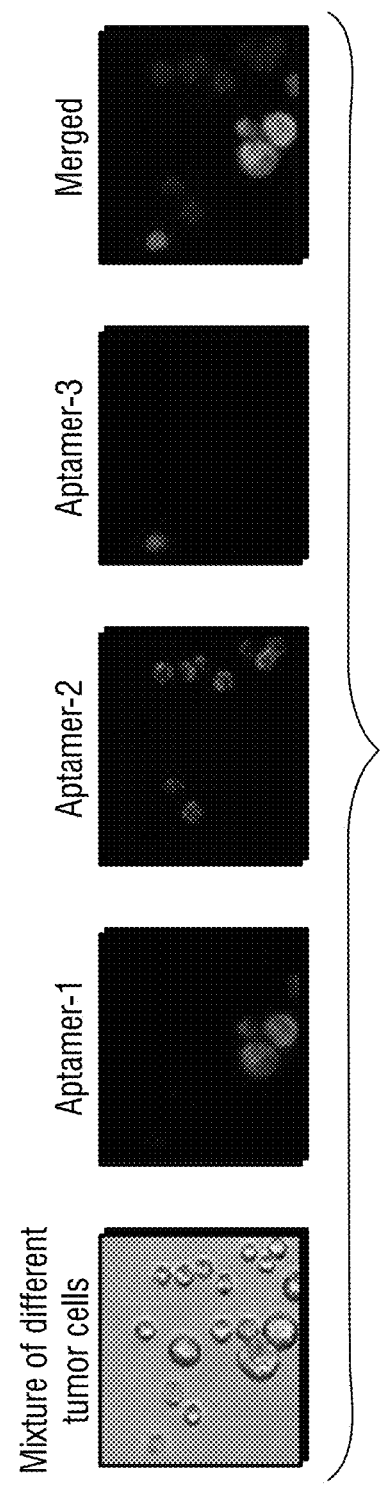
Figure 29B:
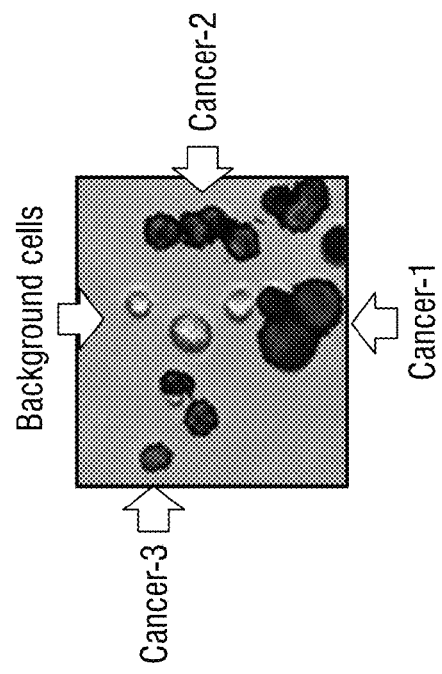
Figure 30:
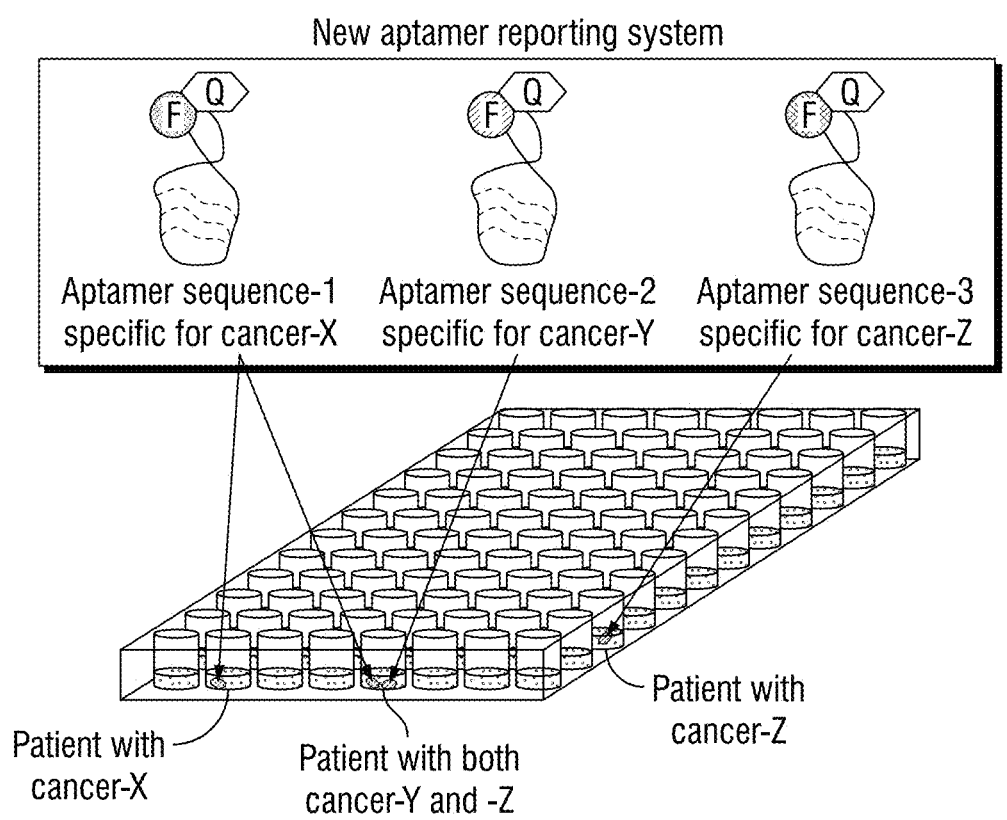

FIG. 27A and FIG. 27B illustrate an exemplary 6-well-plate assay performed in accordance with one aspect of the present invention. In this assay, wells were loaded with 50 µL of whole blood containing diluted lymphoma tumor cells. The entire well was scanned by a Scanner microscope system (Molecular Devices, LLC; Sunnyvale, Calif., USA) and the fluorescent images were composed. FIG. 27A shows the resulting light microscope images under 4× magnification, while FIG. 27B shows the fluorescent imaging of lymphoma tumor cells that were specificailly identified using the disclosed aptamer-based assay (green fluorescence). Notably, high-definition imaging of the cells could be recorded using either 10× or 20× magnification;

FIG. 28A, FIG. 28B, and FIG. 28C show that a mixed population of different aptamer probes could specifically stain particular types of tumor cells in a mixed population of cells without producing background, or off-target staining. In this study, three different types of cultured tumor cells (cancer-1: epithelial cells of breast cancer; cancer-2: endothelial cells of sarcoma tumor; and cancer-3: tumor cells of ALCL lymphoma) were co-incubated with a detection reagent cocktail that included three aptamers, each of which was specific for a different biomarker (aptamer-1 for EPCAM, aptamer-2 for VEGF, and aptamer-3 for CD30), and each of which contained a unique fluorescent reporter. After incubation at room temperature for 30 min, cell assays were directly examined using fluorescence microscopy without any additional preparation steps. Each of the tumor cell-activated aptamers selectively identified tumor cells that expressed the specific biomarkers, but none showed any off-target signals or non-specific binding towards any other type of tumor cells;

FIG. 29A and FIG. 29B demonstrate that multiple tumor cell-activated aptamers could be used in the same assay for simultaneous detection of different type of cancer cells in a single cell mixture. For simultaneous detection of multiple targets in a single sample, three different tumor cell-activated aptamer sequences (aptamer-1, -2, and -3, respectively) were each conjugated to a different fluorescent reporter molecules (FAM, Cy3, and Cy5, respectively) to generate a multi-aptamer detection cocktail. A cell mixture was then prepared by mixing different types of cultured tumor cells (cancer-1, -2, and -3, respectively), added to the multi-aptamer reagent cocktail, and then incubated for 30 minutes at room temperature. Fluorescence microscopic examination revealed that each aptamer selectively highlighted a specific type of tumor cells, but did not cross-react with any of the other types of tumor cells in the same cell mixture (FIG. 29A). These findings demonstrated that using multiple, distinctly-labeled singly-specific aptamers in a single assay could simultaneously be used to detect each of the discreet types of circulating tumor cells within a multi-cell type population of cells that were all present in a single sample (FIG. 29B); and FIG. 30 illustrates an exemplary ODOSA platform for simultaneous detection of different types of circulating tumor cells in a single blood sample by employing a one-step, high-throughput multi-well, platform, that is suitable and scalable to rapid, point-of-care, screening use. By employing unique aptamer sequences that are each conjugated to unique reporter molecules, the ODOSA of the present invention permits simultaneous detection of different type of circulating tumor cells in a single-drop blood specimen, and in a one-step, high throughput fashion. Therefore, this ODOSA technology is suitable for large-scale, "point-of-care" screening at an overall lower cost than conventional, multi-component, multi-step assay systems. Notably, the new ODOSA technology disclosed herein is applicable for detecting any type of circulating tumor cells simply by employing unique aptamer sequences that are specific for each different type of cancers, and are each chemically linked to distinct fluorescent reporters for detection.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Scientists and physicians have long sought to develop a high-throughput technology that can specifically detect circulating tumor cells in a sample as small as a single drop of blood and be carried out as simply as a one-step reaction. The present invention employs unique intra-tumor cell-activatable aptamer probes in a novel One-Drop-One-Step Assay (ODOSA) methodology. In contrast to conventional assay systems, the ODOSA described herein permits the discreet highlighting of tumor cells intracellularly, without producing off-target, or background signals. Moreover, the high-degree of specificity exhibited by the novel ODOSA method permitted the detection of a single circulating tumor cell from among a population of millions of blood cells in a one-step, one-reagent assay, that took only a few minutes to perform.

Aptamers

Aptamers are small-molecule probes composed of short, single-stranded oligonucleotides (typically RNA or ssDNA, and typically from about 30 to about 60 nucleobases in length). Aptamers, which belong to a class of small molecule ligands composed of short single-stranded oligonucleotides, have emerged as probes over the last several decades; however, their potential clinical value has not yet been fully explored. Aptamers may be developed from RNA/ssDNA libraries via a defined experimental process called Systematic Evolution of Ligands by EXponential (SELEX) enrichment (Ellington and Szostak, 1990; Tuerk and Gold, 1990). Synthetic aptamers are able to specifically bind an extremely wide variety of targets, including small molecules (dyes, metal ions, amino acids, and short peptides), biomacromolecules (e.g., nucleic acids and proteins), molecular complexes, viruses, and even live cells. Theoretically, the low nanomolar binding affinities and exquisite specificity of aptamers for their targets make them a versatile tool for disease diagnosis and targeting therapy. Compared to protein antibodies, as a small molecule probe aptamers are easily generated through chemical synthesis and simply modified with a variety of functional groups and/or tracking/imaging reporters. Notably, oligonucleotide aptamers have little or no immunogenicity or toxicity for in vivo use.

Because of their unique three-dimensional (3D) structures, oligonucleotide aptamers can recognize and specifically bind to target biomolecules such as small molecules, biomacromolecules, viruses, living cells, and even whole organisms. As small-molecule probes, aptamers have unparalleled advantages when compared to conventional antibodies, and can be readily and economically prepared by methods such as chemical synthesis. Moreover, the sequences can be conveniently modified using a variety of tracking/imaging reporters and/or functional molecules for different purposes.

Table 1 compares current methods for tumor cell detection with respect to throughput, sensitivity, and obtained results.

TABLE 1

| DETECTION METHOD | THROUGHPUT | SENSITIVITY | RESULTS |
| --- | --- | --- | --- |
| Automated Microscopy | <30 Minutes | Super | Image |
| Microplate Reader | Seconds | High | Signal |
| Scanning Cytometer | Minutes | High | Image |

Labeled Aptamer Probes

Different from current assay systems, the innovative technology herein employs unique intra-tumoral, cell-activatable probes that are composed of a synthetic oligonucleotide aptamer sequence specific for a tumor cell biomarker conjugated to a paired fluorochrome-quencher reporter system. In the absence of tumor cells, the quencher molecule optically silences the paired fluorochrome. However, specific binding of the aptamer probes to tumor cells, subsequent intracellular internalization, and endosomal degradation of the aptamer sequence through natural cellular processes results in the activation of the reporter system. Release of the fluorochrome from the paired quencher molecule will result in bright fluorescent signals exclusively within the targeted tumor cells, thereby allowing highly sensitive and specific detection.

Use of the disclosed ODOSA technology with a suitable fluorescence microscopy-based detection system, permit clinicians and medical professionals for the first time to detect as few as a single circulating tumor cell in a minimal sample volume of patient's blood using a rapid, one-step, multi-sample platform in real time.

Flow Cytometry Analysis Using Labeled Aptamer Probes

In an illustrative embodiment, the inventors synthesized a 39-mer aptamer that specifically binds to CD30 polypeptide with high affinity in solution (SEQ ID NO:1). This representative synthetic aptamer probe contained the essential core sequence for CD30 binding with 5'- and 3'-overhangs, to form a stem structure. For tracking and imaging purposes, the synthetic aptamer sequence was labeled with the fluorochrome, Cy5.5, as a reporter molecule.

First, to determine whether the aptamer probe could be used to detect intact tumor cells, it was incubated with cultured lymphoma tumor cells, and the cell binding was quantified by flow cytometry. This aptamer probe selectively bound intact CD30-expressing tumor cells (Karpas 299, HDLM2, L428, and KMH2) with significantly high affinity (0.3 nM final concentration), but had no or little reaction to lymphoma tumor cells that either did not, or only weakly expressed, the CD30 biomarker (Jurkat, K562, and RPMI8226). Notably, cell-staining patterns of the aptamer probe in all tested cells were identical to those obtained by a CD30-specific antibody based assay (currently the only clinically-validated detection method approved for circulating tumor cell analysis). For further validation, different amounts of lymphoma cells were diluted in fresh marrow blood specimen from healthy donor and this tumor-blood cell mixture was simultaneously incubated with the CD30-specific aptamer-Cy5.5-labeled probe and antibodies that were specific for either CD30 (FITC) or CD45 (PerCP). Flow cytometry revealed that the aptamer probes specifically recognized only CD30-expressing tumor cells, but did not stain any type of blood cells present in marrow samples, including nucleated red blood cells, myeloblasts, granulocytes, lymphocytes, and monocytes. Quantitative analysis demonstrated that the CD30-specific aptamer probe and the CD30-specific antibody detected identical amounts (%) of lymphoma tumor cells in the blood mixture.

Turning to FIG. 1A an idealized assay for rapid tumor detection using a single drop of blood is illustrated. In FIG. 1B, a representative assay in accordance with certain aspects of the present invention employs a "tumor cell-activated" probe that specifically binds to tumor cells without producing any significant levels of "off-target" (i.e., background) signals. FIG. 1C, included as a comparison, illustrates a standard assay from the prior art that uses a constantly "active" probe that, unlike the present design, highlight both tumor cells and off-target signals.

Turning to FIG. 2, an illustrative assay in accordance with one aspect of the present invention is illustrated. This assay utilizes a probe system that is specifically activated (and therefore emits signals) exclusively within tumor cells. The detection probes employed in the present invention include an aptamer sequence portion body that specifically targets biomarkers of tumor cells, and which is operably linked to an "activatable" reporter system (in this case, a pair of fluorochrome and quencher molecules). Under normal conditions, the quencher molecule blocks fluorochrome molecules from binding to the same aptamer, thus rendering it "inactive" or quenched. Specific binding of the labeled aptamer probe, however to target tumor cells leads to an intracellular internalization (and subsequent endosomal degradation) of the aptamer probes. Release of the fluorochrome from the quencher molecule results in an "active" signal exclusively from within the tumor cells. Importantly, this feature of the assay permits specific tumor cells to be labeled, with no "off-target" or background signal being produced.

Turning now to FIG. 3, cultures of exemplary lymphoma tumor cells and cultures of control lymphoma cells were incubated in either the presence, or the absence, of CD30+-specific labeled aptamer probe. Results demonstrated that the labeled aptamer probes were activated exclusively within tumor cells, and thus specifically highlighted CD30+ the tumor cells without producing any background or off-target non-specific signals. The lower row of photographs showed that no off-target signals were detected in the control lymphoma cells that do not express the CD30-specific biomarker. FIG. 4A, FIG. 4B, FIG. 4C, and FIG. 4D illustrate a similar intracellular activation of the aptamer probe, with the merged image (FIG. 4D) demonstrating specificity of the assay.

Turning to FIG. 5A and FIG. 5B, a schematic overview of the one-step assay is illustrated. In its simplest form, a single drop of a biological sample of interest (for example, a patient's blood or other bodily fluid) is sufficient in quantity to permit the detection of a single tumor cell using the assay method described herein. FIG. 5B shows the detection of lymphoma tumor cells following a 20-min incubation specimens were examined by fluorescent microscope (lower row). A single CD30+ lymphoma cell (arrow) was detected among the millions of normal blood cells in the specimen. FIG. 6A, FIG. 6B, FIG. 6C, and FIG. 6D further exemplify a double staining protocol for lymphoma tumor cells. FIG. 6D shows a merged image in which the aptamer probes specifically detected CD30+ lymphoma tumor cells, while an antibody stain detected non-tumor cells.

The inventors contemplate that a key benefit of the one-step assay disclosed herein is the ability to scale-up the process and to automate it via conventional robotic multi-well systems. Turning now to FIG. 7A-FIG. 7C, FIG. 8, and FIG. 9, illustrative protocols are shown for high-throughput, highly-sensitive, and highly-specific assays for detection of aptamer-specific tumor cells from very small samples (including specimens that are only a single drop of blood). The one-step assay system is useful in detecting, inter alia, circulating tumor cells (FIG. 9). One important application of the new assay system is the creation of a high throughput, multi-sample microtiter plate based method suitable for robotic assay applications.

Turning now to FIG. 11, an illustrative synthetic RNA-based CD30 aptamer probe was created having the sequence 5'-gauUCGUAUGGGUGGGAUCGGG AAGGGCUAC-GAACAccg-3' (SEQ ID NO:1). The aptamer was conjugated with fluorochrome Cy5.5 in accordance with one aspect of the present invention and used to detect CD30+-specific antigens. Specific staining of intact ALCL cells by the CD30 aptamer is shown in FIG. 14, and the high affinity of aptamer probe to lymphoma cells that express CD30 biomarker is shown in FIG. 13A, FIG. 13B, FIG. 13C, FIG. 13D, FIG. 13E, and FIG. 13F.

FIG. 14A and FIG. 14B show the specific staining of lymphoma tissues using a synthetic CD30 aptamer probe in accordance with one aspect of the present invention. FIG. 15A and FIG. 15B show a modification of conventional tissue immunostaining using a synthetic CD30 aptamer probe in accordance with one aspect of the present invention.

FIG. 16 demonstrates a schematic of the protocol for specific imaging of xenografted lymphoma tumor by aptamer probe, and FIG. 17 demonstrates results of the specific imaging of xenografted lymphoma tumor by aptamer probe in a rodent animal model. An illustrative aptamer probe is shown in FIG. 18. It has a nucleotide sequence that is specific for tumor cell targeting, operably linked to an "intra-tumor cell activatable" reporter system that is composed of a pair of fluorochrome-quencher molecules. In the absence of the "target" tumor cells, the fluorochrome is optically silenced ("inactive") by the paired quencher molecule, and no signal is observed. FIG. 22 also illustrates exemplary reporter systems having different pairs of fluorochrome-quencher molecules that may be used in the ODOSA methods disclosed herein.

Turning to FIG. 19A and FIG. 19B, the inventors demonstrated that optical activation of the aptamer probes in tumor cell lysates was not due to low pH conditions, and in FIG. 20A and FIG. 20B they demonstrated successful diagnosis of anaplastic large T-cell lymphoma tumor in a tissue sample due to the specific binding of the CD30+-specific aptamer to CD30+-expressing tumor cells.

FIG. 21 shows an illustrative "intra-tumor cell activatable" aptamer probe useful in the practice of the invention. The reporter system is optically silent in the absence of tumor cells. The sequence of the aptamer was specific for the tumor cell-binding core sequence and stem sequence, and its length was selected for the ability of the quencher to silence the reporter fluorochrome in its native form. Similarly, FIG. 23 illustrates an example of optimizing a particular aptamer sequence by the addition of 5" and/or 3' bases to yield a variety of probe sizes (34 to 72-mer) (SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO:11, respectively) to provide the highest binding affinity/specificity to CD30-expressing tumor cells with the lowest background signal.

Turning to FIG. 24A and FIG. 24B, specific binding of exemplary ssDNA aptamers specific for CD30-expressing cells was demonstrated, while no aptamer binding was observed in control cells that lacked CD30 expression.

FIG. 25, FIG. 26, FIG. 27A and FIG. 27B illustrate fluorescent signal recordation in a digital format using a BioTek microplate reader, an exemplary ODOSA platform for simultaneous detection of different circulating tumor cells in a single blood sample, and an exemplary 6-well-plate assay performed in accordance with one aspect of the present invention, respectively. In representative assays, wells were loaded with 50 µL of whole blood containing diluted lymphoma tumor cells. The entire well was scanned (Molecular Devices) as described herein, and the fluorescent images were composed. FIG. 27A shows the resulting light microscope images under 4× magnification, while FIG. 27B shows the fluorescent imaging of lymphoma tumor cells that were specifically identified using the disclosed aptamer-based assay (green fluorescence). Notably, high-definition imaging of the cells could be recorded using either 10× or 20× magnification;

FIG. 28A, FIG. 28B, and FIG. 28C show that a mixed population of different aptamer probes could specifically stain particular types of tumor cells in a mixed population of cells without producing background, or off-target staining. In this study, three different types of cultured tumor cells (cancer-1: epithelial cells of breast cancer; cancer-2:

endothelial cells of sarcoma tumor; and cancer-3: tumor cells of ALCL lymphoma) were co-incubated with a detection reagent cocktail that included three aptamers, each of which was specific for a different biomarker (aptamer-1 for EPCAM, aptamer-2 for VEGF, and aptamer-3 for CD30), and each of which contained a unique fluorescent reporter. After incubation at room temperature for 30 min, cell assays were directly examined using fluorescence microscopy without any additional preparation steps. Each of the tumor cell-activated aptamers selectively identified tumor cells that expressed the specific biomarkers, but none showed any off-target signals or non-specific binding towards any other type of tumor cells;

Multiple tumor cell-activated aptamers may be developed and used in the disclosed assay for the simultaneous detection of different type of cancer cells in a single cell mixture. In FIG. 29A and FIG. 29B simultaneous detection of multiple targets in a single sample is illustrated. Here, three different tumor cell-activated aptamer sequences (aptamer-1, -2, and -3, respectively) were each conjugated to different fluorescent reporter molecules (FAM, Cy3, and Cy5, respectively). This multi-labeled aptamer "cocktail" could then be used to identify each aptamer-specific target in a mixed population of cells. Fluorescence microscopic examination revealed that each aptamer specifically bound to, and thus, selectively identified, a particular type of tumor cell. Importantly, none of the labeled aptamers cross-reacted with any of the other types of tumor cells in the same cell mixture. These findings demonstrated that using multiple, distinctly-labeled singly-specific aptamers in a single assay could simultaneously be used to detect each of the discreet types of circulating tumor cells within a multi-cell type population of cells that were all present in a single sample.

Turning to FIG. 30, in another illustrative embodiment, an ODOSA platform is provided for simultaneous detection of different types of circulating tumor cells in a single blood sample. Employing a one-step, high-throughput multi-well, platform that is both suitable and scalable, facilitates rapid, cost-effective, point-of-care screening and testing. By employing unique aptamer sequences that are each conjugated to unique reporter molecules, the ODOSA of the present invention permits simultaneous detection of different type of circulating tumor cells in a single-drop blood specimen, and in a one-step, high throughput fashion.

EXEMPLARY DEFINITIONS

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the relevant arts. Singleton et al., (1994) and Hale and Markham (1991) are examples of references that provide one of ordinary skill with the general meaning of many of the terms used herein. A detailed discussion of the differences and similarities between shRNA and siRNA molecules can be found in Rao et al., 2009). Each of these references is specifically incorporated herein in its entirety by express reference thereto. Still, certain terms are defined below for the sake of clarity and ease of reference.

In accordance with long standing patent law convention, the use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert (s), or such like, or a combination thereof that is pharmaceutically acceptable for administration to the relevant animal or acceptable for a therapeutic or diagnostic purpose, as applicable.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

As used herein, "an effective amount" would be understood by those of ordinary skill in the art to provide a therapeutic, prophylactic, or otherwise beneficial effect.

The term "e.g.," as used herein, is used merely by way of example, without limitation intended, and should not be construed as referring only those items explicitly enumerated in the specification.

As used herein, the term "expression" refers to the process by which a polypeptide is produced based on the nucleic acid sequence of a gene. The process includes both transcription and translation.

The phrase "expression control sequence" refers to any genetic element (e.g., polynucleotide sequence) that can exert a regulatory effect on the replication or expression (transcription or translation) of another genetic element. Common expression control sequences include promoters, polyadenylation (polyA) signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

The term "heterologous" refers to elements that are not normally associated with each other. For example, if a host cell produces a heterologous protein, that protein is not normally produced in that host cell. Likewise, a promoter that is operably linked to a heterologous coding sequence is a promoter that is operably linked to a coding sequence that it is not usually operably linked to in a wild-type host cell. The term "homologous," with reference to a polynucleotide or protein, refers to a polynucleotide or protein that occurs naturally in a host cell.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The term "hybridization" refers to the process by which a strand of nucleic acid joins with a complementary strand through base pairing as known in the art. A given nucleic acid is "selectively hybridizable" to a reference nucleic acid sequence if the two sequences specifically hybridize to one another under moderate to high stringency hybridization and wash conditions. Moderate and high stringency hybridization conditions are known to those of ordinary skill in the molecular biology arts (see, e.g., Ausubel et al., 1995 or Sambrook et al., 2001). Each of these references is incorporated herein in its entirety by express reference thereto.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, the term "kit" may be used to describe variations of the portable, self-contained enclosure that includes at least one set of reagents, components, or pharmaceutically-formulated compositions to conduct one or more of the therapeutic methods of the invention. Optionally, such kit may include one or more sets of instructions for use of the enclosed reagents, such as, for example, in a laboratory or clinical application.

Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally-occurring animals.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, the term "patient" (also interchangeably referred to as "host" or "subject") refers to any host that can serve as a recipient of one or more of the therapeutic or diagnostic formulations as discussed herein. In certain aspects, the patient is a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

The phrase "pharmaceutically acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N' dibenzylethylenediamine or ethylenediamine; and combinations thereof The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

A "plurality" contains at least two members. In certain cases, a plurality may have at least 10, at least 100, at least 1000, at least 10,000, at least 100,000, or at least 1,000,000 or more members.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

The term "promoter," as used herein refers to a region or regions of a nucleic acid sequence that regulates transcription.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of from about 2 to about 20 amino acid residues in length, oligopeptides of from about 10 to about 100 amino acid residues in length, and polypeptides including about 100 amino acid residues or more in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "promoter" refers to a regulatory sequence that initiates transcription of a downstream nucleic acid. The term "operably-linked" refers to an arrangement of elements that allows them to be functionally related. For example, a promoter is operably-linked to a coding sequence if it controls the transcription of that sequence.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99% sequence identity between the selected sequence and the reference sequence to which it was compared.

The percentage of sequence identity may be calculated over the entire length of the sequences to be compared, or may be calculated by excluding small deletions or additions which total less than about 25% or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

As used herein, the term "structural gene" is intended to generally describe a polynucleotide, such as a gene, that is expressed to produce an encoded peptide, polypeptide, protein, ribozyme, catalytic RNA molecule, or antisense molecule.

"Transcriptional regulatory element" refers to a polynucleotide sequence that activates transcription alone or in combination with one or more other nucleic acid sequences. A transcriptional regulatory element may include, for example, one or more promoters, one or more response elements, one or more negative regulatory elements, one or more enhancers, or any combination thereof As used herein, a "transcription factor recognition site" and a "transcription factor binding site" refer to a polynucleotide sequence(s) or sequence motif(s) that are identified as being sites for the sequence-specific interaction of one or more transcription factors, frequently taking the form of direct protein-DNA binding. Typically, transcription factor binding sites can be identified by DNA footprinting, gel-mobility shift assays, and the like, and/or can be predicted based on known consensus sequence motifs, or by other methods known to one of ordinary skill in the relevant molecular biological and virology arts.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the term "vector" refers to a nucleic acid molecule capable of transporting another nucleic acid to which it has been linked, e.g., a plasmid. One type of preferred vector is an episome, i.e., a nucleic acid capable of extra-chromosomal replication. Preferred vectors are those capable of autonomous replication and/or expression of nucleic acids to which they are linked.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardt's solution, 5×SSC, 25 mM sodium phosphate, 0.1% SDS and 100 µg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardt's solution, 5×SSC, 25 mM sodium phosphate, 0.1% SDS and 100 µg/ml denatured salmon sperm DNA or E. coli DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence.

Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

EXAMPLES

The following examples are included to demonstrate illustrative embodiments of the invention. It should be appreciated by those of ordinary skill in the art that the techniques disclosed in this example represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1

Tumor Cell Detection Assay System

To develop an exemplary assay system with significant potential for clinical application, RNA-based aptamers that are specific for one or more cellular biomarkers (e.g., CD30 protein) were synthesized (Zhang et al., 2009) and each were conjugated to a specific fluorochrome reporter molecule (such as Cy 3, Cy5.5, etc.) operably linked to a quencher molecule (e.g., BHQ2).

Freshly cultured CD30-positive lymphoma cells (ATCC, Manassas, Va., USA) were stained with the aptamer probes or anti-CD30 antibody (BD Biosciences) as a standard control. Flow cytometry analysis showed that the aptamer probe is able to selectively bind to and detect lymphoma cells that express CD30 (Zhang et al., 2009). Specific cell binding of aptamer probes was also confirmed by fluorescence microscopy at a final concentration as low as 0.3 nM. Multicolor flow cytometry demonstrated that comprehensive immunophenotyping of lymphoma cells could be performed by using oligonucleotide aptamer probe(s) in combination with different antibodies as showed in our previous publication (Zhang et al., 2009).

Subsequently, the use of synthetic aptamers for immunohistochemical study of formalin-fixed and paraffin-embedded tumor tissues (including anaplastic large cell lymphoma and classical Hodgkin lymphoma) was also validated as previously published (Zeng et al., 2010). For this purpose, the selected aptamers were biotinylated (Integrated DNA Technologies, Coralville, Iowa), and a horseradish peroxidase (HRP)-conjugated streptavidin system (Dako) was employed for visualization of the immunohistochemical staining Tumor tissue studies revealed that the aptamer probes specifically recognized and selectively immunostained CD30-positive tumor cells of classical Hodgkin lymphoma and anaplastic large cell lymphoma, but did not react with background cells (FIG. 20A and FIG. 20B). The aptamer probe optimally immunostained lymphoma cells with lower temperature antigen retrieval and shorter probing reaction times than typical antibody immunohistochemical protocols.

In necrotic tumor tissues, the aptamer probe showed no non-specific background staining of cell debris although antibody-medicated immunohistochemical staining often does (FIG. 21).

In addition, for in vivo lymphoma detection, a tumor-bearing mouse model was established (FIG. 23), each mouse has both CD30-positive and CD30-negative control lymphoma tumors. The synthetic aptamer was conjugated with Cy5.5 reporter (Integrated DNA Technologies, Coralville, Iowa, USA) and administered into the mice systemically. Imaging studies demonstrated that the aptamer probes selectively highlighted lymphoma tumor that expresses CD30, but not control tumor in the same mouse. The highest imaging signal in tumor site was detected in 10 min post aptamer probe administration and the imaging signal completely disappeared from mouse body within 3 hours (FIG. 24).

The observed tumor imaging by aptamer probes was confirmed by histology examination of the removed tumor tissues post imaging study.

In summary, these findings show first demonstration that synthetic oligonucleotide aptamer can be used for both in vitro detection and in vivo imaging study of lymphoma.

Materials

Synthetic 32-base RNA oligonucleotide CD30-specific aptamer probe (sequence is shown in FIG. 4B). Quencher molecule: BHQ2 (Integrated DNA Technologies); Fluorochrome: Cy3 (Integrated DNA Technologies); CD30-positive lymphoma cell line: Karpas 299 (American Type Culture Collection, Manassas, Va., USA); CD30-negative lymphoma cell line: U937 (American Type Culture Collection).

Experimental Methods

In Vitro Analysis of Aptamer-Based Detection Probes

To demonstrate the efficacy of the new assay system, cultured cells were incubated with the aptamer probes (5 nM final concentration) for 30 min, and cell signals were then evaluated by florescence microscopy. As shown in FIG. 7, the assay specifically identified (i.e., "highlighted") CD30+ lymphoma tumor cells, but did not react with control lymphoma cells that lacked the CD30 biomarker. Importantly, no background signals were detected in the assays using the inactive aptamer probe alone (FIG. 28 and FIG. 29).

In addition, lymphoma cell membrane was pre-stained with Alexa Fuor® 488 green fluorescent dye (Sigma-Aldrich, St. Louis, Mo., USA) and then incubated with the aptamer probes. Fluorescence microscopy confirmed the exclusively intracellular illuminating of fluorescent signals (red) (FIG. 25).

Analysis on Patient Blood Samples

To demonstrate utility of the assay on actual clinical samples, a blood specimen from a patient who had a CD30+ anaplastic large cell lymphoma was obtained. A drop of this blood was directly mixed with a CD30-specific aptamer-reporter (FIG. 4B), incubated at room temperature for 20 min, and examined by fluorescence microscopy. The one-step assay revealed the rare lymphoma tumor cells with high sensitivity, and could single circulating tumor cell among millions of normal blood cells (FIG. 8, FIG. 29, and FIG. 31).

As a confirmation, the patient's blood cells were subsequently stained with both CD30 antibody (conjugated with FITC in green) (BD Biosciences, San Jose, Calif., USA) and the aptamer-reporter (red fluorescent) (FIG. 4B). The merged image confirmed that the aptamer-reporter probes specifically detected CD30+ lymphoma tumor cells (FIG. 7).

These data demonstrated a new, one-step, cell detection system that was tumor cell-specific, highly sensitive, and able to intracellularly highlight the cells of interest without the production of off-target (i.e., background) signals.

By adapting the present system using additional cell type-specific aptamer probes, a variety of new clinical tests can now be commercialized that specifically identify different circulating tumor cells. Such applications include, without limitation, the analysis of tumor stem cells, as well as cancers of mammalian blood, breast, prostate, lung, colon, stomach, etc.

Standardization and adaption of the assay system to employ a robotic protocol further extend the usefulness of the present detection reagents and methodologies in both diagnostic laboratories and clinical settings, including but not limited to 1) simultaneous multiple sample detection; 2) rapid high throughput load-then-read screening assay; 3) simultaneous detection of different type of tumor cells in a single sample.

Example 2

Aptamer Probes as Replacements for Conventional Antibody-Based Diagnostics

In this example, the use of a synthetic aptamer probe for cell immunophenotyping, tissue immunohistochemical (IHC) stain, and blood circulating tumor cell detection was demonstrated.

Experimental Methods

For immunophenotyping a CD30-specific aptamer probe (FIG. 4A) was synthesized and conjugated with a fluorochrome Cy5.5 reporter. Cultured lymphoma cells as showed in FIG. 16 were stained with the aptamer probe in combination with antibodies and analyzed by multicolor flow cytometry as published previously (Zhang et al., 2009). For tissue IHC study, biotinylated aptamer probes were generated (Integrated DNA Technologies, Coralville, Iowa, USA). Formalin-fixed and paraffin-embedded lymphoma tissues were stained with the aptamer probes (FIG. 17) and visualized by a HRP-conjugated streptavidin color development kit (Dako).

For circulating tumor cell detection a novel "intracellular-activatable" assay system was developed by conjugating aptamer probe with both fluorochrome and corresponding quencher molecule (FIG. 4B). Under normal condition, quencher molecule interacts with fluorochrome present in the same aptamer probe and renders it "inactive" (FIG. 4C).

Aptamers for Immunohistochemical Detection of Lymphoma Tumors

To detect lymphoma tumor cells on the formalin-fixed and paraffin embedded tissue, a CD30-specific aptamer probe was synthesized and biotinylated at the 5'-end by replacing the Cy5.5 reporter fluorochrome (Zeng et al., 2010). For visualization, the HRP-conjugated streptavidin and DAB peroxidase substrate system was employed (Dako). Tissue sections of Hodgkin lymphoma tumors were stained by the aptamer probe and antibody under the same conditions (FIG. 17). These studies were the first to demonstrate that the aptamer probes could specifically immunostain lymphoma tumor cells with an identical pattern to that of CD30-specific antibodies under the same conditions, and not react to background cells within tumor tissues (FIG. 18 and FIG.

20). In addition, the aptamer probe did not show any non-specific staining background in other types of tumors or normal tissues (FIG. 21).

Example 3

Design of "Intra-Tumor Cell-Activatable" Aptamer Probes

To develop the one-step assay technology for circulating tumor cell detection, the inventors chose to use aptamers instead of traditional antibody probes for target recognition and signal reporting. Aptamer sequences were synthesized, and conjugated to the fluorochrome Cy3 (Integrated DNA Technologies) and quencher BHQ2 molecules (Integrated DNA Technologies) at the 5'- and 3' ends, respectively (FIG. 4B). Notably, in the absence of cells of interest, the aptamer probes are optically silent (i.e., "inactive"), because the fluorochrome is completely quenched/inactivated by the paired quencher molecule that is present on the same aptamer molecule (FIG. 4C). After specifically binding to targeted tumor cells and being internalized, however, subsequent lysosomal degradation of the aptamer sequence activates the previously-optically-silent reporter system by freeing the fluorochrome from the paired quencher molecule, resulting in bright fluorescent signals that are localized exclusively within the target tumor cells (FIG. 2 and FIG. 3).

As a one-step assay, the aptamer-reporters were simply added into cultures of CD30-expressing lymphoma tumor cells. Without any additional steps, cell staining was directly examined by fluorescence microscopy at different time points as indicated. Tumor cells were highlighted with intracellular fluorescent signal and no background. Signals were observed from 10 min, reached maxima at 30 min, and lasted longer than 120 min.

For specificity validation, different lymphoma tumor cells were incubated with the same aptamer probe at room temperature for 30 min, and the resultant cell staining was examined by fluorescence microscopy. As expected, the labeled aptamer probes specifically highlighted the known CD30-expressing lymphoma tumor cells, but did not react to control cells that did not express the CD30 biomarker.

Aptamer Probes are Internalized into Tumor Cells and Co-Located with Cell Lysosomes In this study, lymphoma tumor cells were pre-stained with Fluorochrome Alexa 488 (Sigma-Aldrich, Inc. St. Louis, Mo.) for membrane labeling and incubated with an aptamer-reporter. Cells were then examined with a confocal fluorescence microscope. Merging of cell membrane image (green) and the aptamer probe image (red) demonstrated that the aptamer probes were internalized and optically activated exclusively within tumor cells. In addition, tumor cells were pre-stained with Lyso-ID dye (green) (Sigma-Aldrich, Inc.) for cell lysosome labeling and incubated with the aptamer-reporter. Merging of the resulting confocal images revealed that the aptamer signals (red) were collocated with cell lysosomes (green), indicating the internalization of the aptamer probes into cell lysosomes.

Aptamer Probes can be Optically Activated by Tumor Cell Lysates

To confirm molecular mechanism of the activation, the aptamer-reporter was incubated with fresh lysates of Karpas 299 tumor cells in a 96-well black wall microplate. Changes in the fluorescent intensity were kinetically monitored by Synergy H4 microplate reader (BioTek, Winooski, Vt., USA). Similar to other findings reported herein, the aptamer-reporter were optically activated in tumor cell lysates with gradually increasing fluorescent signals over time. In the control experiment, an aptamer probe conjugated to the same fluorochrome alone with no quencher molecule, showed no change in fluorescent signal density.

In addition, to rule out potential pH effects, the aptamer probes were incubated in PBS buffers with different pH from 4 to 7.4 and changes in fluorescent density were kinetically monitored. Low pH had no effect on the aptamer probes. These findings indicated that the aptamer-reporter was optically activated by degradation, and not because of the low pH within the lysosome itself.

Highly-Sensitive, Aptamer Probes are Specific for Tumor Cell Detection

To prepare a cell mixture, CD30-expressing Karpas 299 lymphoma tumor cells were diluted in pre-stained (membrane) CD30-negative tumor cells. The aptamer-reporters (5 nM) were added into cell mixtures with different dilutions of tumor cells (up to 1/10,000 dilution). After incubation for 30 min at room temperature, cell mixtures were examined by fluorescent microscope. Merging of control cell images (green) and tumor cells that were highlighted in red demonstrated that the aptamer probes was able to specifically detect one single tumor cell among 10,000 background cells.

Example 4

ODOSA Using Whole Blood Sample from a Lymphoma Patient

A patient who was diagnosed with anaplastic, large T-cell lymphoma was selected. Excisional biology of the patient's lymph node mass showed characteristic lymphoma tumor cells by H&E stain, and CD30 expression was confirmed by immunohistochemistry. For staging purposes, blood and bone marrow aspirate were also tested by flow cytometry analysis using a CD30-specific antibody. No circulating lymphoma tumor cells, however, were detected. This was most likely due to the fact that 1) tumor cells of anaplastic large T-cell lymphoma and Hodgkin lymphoma vary widely in size and thus do not form a distinct cluster on cytometry plots; and/or 2) as with other solid carcinoma tumors, anaplastic large T-cell lymphoma may release such a low number of circulating tumor cells into blood or marrow that it is beyond the detection capacity of current flow cytometry technology.

60 μL (conveniently approximated to "one drop") of the patient's whole blood was loaded into a 12-well plate which was pre-loaded with the optically-silent aptamer-reporter at 5 nM final concentration. After incubation at room temperature for 30 min, the plate was directly examined by fluorescence microscopy. As expected, circulating lymphoma tumor cells were detected in some of wells using the one-step assay. Notably, this technology was able to detect one single circulating tumor cell among ≥200 million total blood cells with no off-target or background noise. Additionally, circulating tumor cells were also detected in the patient's bone marrow aspirate sample, at a slightly higher incidence.

Results

Flow cytometry showed that the synthetic CD30 aptamer probe specifically stained anaplastic large cell lymphoma and Hodgkin lymphoma cells, but not control lymphoma cells that do not express CD30. Cell staining patterns of the aptamer probe were identical to that by CD30 antibody. Tissue IHC stains showed that the aptamer probe specifically recognized CD30-positive lymphoma tumor cells, but did not react to normal background cells within tumor sites. The aptamer probe could efficiently stain tissues within shorter time than standard antibody.

To translate the ODOSA system with a novel aptamer-reporter system described herein into clinical use, validation of the technology was accomplished using actual clinical specimens, such as blood and marrow aspirate obtained from cancer patients. Studies showed that the ODOSA system could be used to specifically detect circulating tumor cells in whole blood, as well as marrow aspirate.

REFERENCES

The following references, to the extent that they provide exemplary procedural or other details supplementary to those set forth herein, are specifically incorporated herein in their entirety by express reference thereto:

AUSUBEL, F J et al., "SHORT PROTOCOLS IN MOLECULAR BIOLOGY," 3rd Ed., Wiley & Sons, New York, N.Y. (1995).

ALLARD, W J et al., "Tumor cells circulate in the peripheral blood of all major carcinomas but not in healthy subjects or patients with nonmalignant diseases," Clin. Cancer Res., 10(20):6897-6904 (October 2004).

ALUNNI-FABBRONI, M and SANDRI, M T, "Circulating tumour cells in clinical practice: methods of detection and possible characterization," Methods, 50(4):289-297 (April 2010).

ATTARD, G et al., "Characterization of ERG, AR and PTEN gene status in circulating tumor cells from patients with castration-resistant prostate cancer," Cancer Res., 69(7):2912-2918 (April 2009).

BALASUBRAMANIAN, P et al., "Confocal images of circulating tumor cells obtained using a methodology and technology that removes normal cells," Mol. Pharm., 6(5):1402-1408 (September-October 2009).

BLANK, M and BLIND, M, "Aptamers as tools for target validation," Curr. Opin. Chem. Biol., 9(4):336-342 (August 2005).

BRODY, E N and GOLD, L, "Aptamers as therapeutic and diagnostic agents," J. Biotechnol., 74(1):5-13 (March 2010).

BUNKA, D H and STOCKLEY, P G, "Aptamers come of age at last," Nat. Rev. Microbiol., 4(8):588-596 (August 2006).

BURKE, D H and GOLD, L, "RNA aptamers to the adenosine moiety of S-adenosyl methionine: structural inferences from variations on a theme and the reproducibility of SELEX," Nucleic Acids Res., 25(10):2020-2024 (May 1997).

CERCHIA, L et al., "Nucleic acid aptamers in cancer medicine," FEBS Lett., 528(1-3):12-16 (September 2002).

CRISTOFANILLI, M et al., "Circulating tumor cells, disease progression, and survival in metastatic breast cancer," N. Engl. J. Med., 351(8):781-791 (August 2004).

DAVIS, K A et al., "Staining of cell surface human CD4 with 2'-F-pyrimidine-containing RNA aptamers for flow cytometry," Nucleic Acids Res., 26(17):3915-3924 (September 1998).

ELLINGTON, A D and SZOSTAK, J W, "In vitro selection of RNA molecules that bind specific ligands," Nature, 346(6287):818-822 (August 1990).

GASCOYNE, P R et al., "Isolation of rare cells from cell mixtures by dielectrophoresis," Electrophoresis, 30(8):1388-1398 (April 2009).

HALE, W G and MARGHAM, J P, "THE HARPER COLLINS DICTIONARY OF BIOLOGY," Harper Perennial, New York, N.Y. (1991).

HERMANN, T and PATEL, D J, "Adaptive recognition by nucleic acid aptamers," Science, 287(5454):820-825 (February 2000).

HEYDUK, T and HEYDUK, E, "Molecular beacons for detecting DNA binding proteins," Nat. Biotechnol., 20(2):171-176 (February 2002).

HUANG, C J et al., "Integrated microfluidic system for rapid screening of CRP aptamers utilizing systematic evolution of ligands by exponential enrichment (SELEX)," Biosens. Bioelectron., 25(7):1761-1766 (March 2010).

JAROSCH, F et al., "In vitro selection using a dual RNA library that allows primerless selection," Nucleic Acids Res., 34(12):e86 (July 2006).

JAYASENA, S D, "Aptamers: an emerging class of molecules that rival antibodies in diagnostics," Clin. Chem., 45(9):1628-1650 (September 1999).

LIU, M C et al., "Circulating tumor cells: a useful predictor of treatment efficacy in metastatic breast cancer," J. Clin. Oncol., 27(31):5153-5159 (November 2009).

LU, J et al., "Isolation of circulating epithelial and tumor progenitor cells with an invasive phenotype from breast cancer patients," Int. J. Cancer, 126(3):669-683 (February 2010).

MAHESWARAN, S et al., "Detection of mutations in EGFR in circulating lung-cancer cells," N. Engl. J. Med., 359:366-377 (July 2008).

MAIRAL, T et al., "Aptamers: molecular tools for analytical applications," Anal. Bioanal. Chem., 390(4):989-1007 (February 2008).

MILLER, M C et al., "Significance of circulating tumor cells detected by the CellSearch system in patients with metastatic breast colorectal and prostate cancer," J. Oncol., 2010:617421 (December 2010).

MORI, T et al., "RNA aptamers selected against the receptor activator of NF-kappaB acquire general affinity to proteins of the tumor necrosis factor receptor family," Nucleic Acids Res., 32(20):6120-6128 (November 2004).

NAGRATH, S et al., "Isolation of rare circulating tumour cells in cancer patients by microchip technology," Nature, 450:1235-1239 (December 2007).

OLIPHANT, A R et al., "Defining the sequence specificity of DNA-binding proteins by selecting binding sites from random-sequence oligonucleotides: analysis of yeast GCN4 proteins," Mol. Cell Biol., 9(7):2944-2949 (July 1989).

PARIS, P L et al., "Functional phenotyping and genotyping of circulating tumor cells from patients with castration resistant prostate cancer," Cancer Lett., 277(2):164-173 (May 2009).

RAO, D D et al., "siRNA vs. shRNA: similarities and differences," Adv. Drug. Deliv. Rev., 61(9):746-759 (July 2009)

RIETHDORF, S et al., "Detection of circulating tumor cells in peripheral blood of patients with metastatic breast cancer: a validation study of the CellSearch system," Clin. Cancer Res., 13:920-928 (February 2007).

SAMBROOK, J et al., "MOLECULAR CLONING: A LABORATORY MANUAL," 3rd Ed., Cold Spring Harbor Laboratory Press, Cold Spring Harbor, N.Y. (2001).

SEFAH, K et al., "Development of DNA aptamers using Cell-SELEX," Nat. Protoc., 5(6):1169-1185 (June 2010).

SEQUIST, L V et al., "The CTC-chip: an exciting new tool to detect circulating tumor cells in lung cancer patients," J. Thorac. Oncol., 4(3):281-283 (March 2009).

SHANGGUAN, D et al., "Aptamers evolved from live cells as effective molecular probes for cancer study," *Proc. Nat'l. Acad. Sci. USA*, 103(32):11838-11843 (August 2006).

SHI, H et al., "Activatable aptamer probe for contrast-enhanced in vivo cancer imaging based on cell membrane protein-triggered conformation alteration," *Proc. Nat'l. Acad. Sci. USA*, 108(10):3900-3905 (March 2011).

SINGLETON et al., "*DICTIONARY OF MICROBIOLOGY AND MOLECULAR BIOLOGY,*" 2$^{nd}$ Ed., John Wiley and Sons, New York, N.Y. (1994).

STOLTENBURG, R et al., "SELEX—a (r)evolutionary method to generate high-affinity nucleic acid ligands," *Biomol. Eng.*, 24(4):381-403 (October 2007).

STOTT, S L et al., "Isolation of circulating tumor cells using a microvortex-generating herringbone-chip," *Proc. Nat'l. Acad. Sci. USA*, 107(43):18392-18397 (October 2010).

STOTT, S L et al., "Isolation and characterization of circulating tumor cells from localized and metastatic prostate cancer patients," *Sci. Transl. Med.*, 2(25):25ra23 (March 2010).

SWENNENHUIS, J F et al., "Characterization of circulating tumor cells by fluorescence in situ hybridization," *Cytometry A.*, 75(6):520-527 (June 2009).

TALASAZ, A H et al., "Isolating highly enriched populations of circulating epithelial cells and other rare cells from blood using a magnetic sweeper device," *Proc. Nat'l. Acad. Sci. USA*, 106(10):3970-3975 (March 2009).

TAN, W et al., "Molecular beacons: a novel DNA probe for nucleic acid and protein studies," *Chemistry*, 6(7):1107-1111 (April 2000).

TUERK, C and GOLD, L, "Systematic evolution of ligands by exponential enrichment: RNA ligands to bacteriophage T4 DNA polymerase," *Science*, 249(4968):505-510 (August 1990).

TYAGI, S et al., "Multicolor molecular beacons for allele discrimination," *Nat. Biotechnol.*, 16(1):49-53 (January 1998).

TYAGI, S and KRAMER, F R, "Molecular beacons: probes that fluoresce upon hybridization," *Nat. Biotechnol.*, 14(3):303-308 (March 1996).

ULRICH, H and WRENGER, C, "Disease-specific biomarker discovery by aptamers," *Cytometry A.*, 75(9):727-733 (September 2009).

WEIGHT, R M et al., "Detection of circulating melanoma cells in human blood using photoacoustic flowmetry," *Conf Proc. IEEE Eng. Med. Biol. Soc.*, 2009:106-109 (2009).

YANG, L et al., "Optimization of an enrichment process for circulating tumor cells from the blood of head and neck cancer patients through depletion of normal cells," *Biotechnol. Bioeng.*, 102(2):521-534 (February 2009).

ZENG, Z et al., "Using oligonucleotide aptamer probes for immunostaining of formalin-fixed and paraffin-embedded tissues," *Mod. Pathol.*, 23(12):1553-1558 (December 2010).

ZHANG, P et al., "Combination of an aptamer probe to CD4 and antibodies for multicolored cell phenotyping," *Am. J. Clin. Pathol.*, 134(4):586-593 (October 2010).

ZHANG, P et al., "Using an RNA aptamer probe for flow cytometry detection of CD30-expressing lymphoma cells," *Lab. Invest.*, 89(12):1423-1432 (December 2009).

It should be understood that the examples and embodiments described herein are for illustrative purposes only and that various modifications or changes in light thereof will be suggested to persons skilled in the art and are to be included within the spirit and purview of this application and the scope of the appended claims.

All references cited herein (including publications, patent applications and patents) are hereby incorporated by reference to the same extent as if each reference was individually and specifically indicated to be incorporated by reference and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order, unless otherwise indicated herein, or otherwise clearly contradicted by context.

The use of any and all examples, or exemplary language (e.g., "such as") provided herein, is intended merely to better illustrate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising," "having," "including," or "containing," with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for detecting a biomarker of interest in a biological sample, comprising contacting the sample with a reporter system that comprises:
   1) a first aptamer probe sequence that specifically targets a first biomarker of interest operably linked to a first reporter pair that includes a first donor moiety operably linked to a first acceptor moiety, such that the first acceptor moiety silences the first donor moiety in its native, or inactive, state,
   under conditions effective, and for a time sufficient, to detect the biomarker of interest in the biological sample, wherein the first aptamer probe sequence consists of the nucleic acid sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

2. The method of claim 1, wherein the first donor moiety comprises a fluorescent, chromogenic, or a biotinylated label.

3. The method of claim 2, wherein the fluorescent label comprises 6-carboxyfluorescein (6-FAM), HEX, R-phycoerythrin (R-PE), tetramethylrhodamine (TRITC), 5-carboxytetramethylrhodamine (5-TAMRA), a cyanine dye, an infrared dye, a Texas red dye, rhodamine, a Rox reference dye, or any combination thereof.

4. The method of claim 3, wherein the first donor moiety comprises a cyanine dye selected from the group consisting of Cy2, Cy3, Cy3.5, Cy5, Cy5.5, Cy7, Cy7.5, and sulfonated derivatives thereof.

5. The method of claim 1, wherein the first acceptor moiety comprises a quencher.

6. The method of claim 5, wherein the first acceptor moiety comprises a quencher selected from the group consisting of Dabcyl, a black hole quencher dye, a Cy5Q NHS ester, a Cy7Q NHS ester, an infrared non-fluorescent dark quencher dye, and combinations thereof.

7. The method of claim 1, wherein the biological sample comprises mammalian blood.

8. The method of claim 1, wherein the biomarker of interest is specific for a circulating mammalian tumor cell or a mammalian cancer cell.

9. The method of claim 1, wherein the biomarker of interest is specific for one or more particular cell types.

10. The method of claim 1, wherein the volume of the sample is between about 10 μL and about 300 μL.

11. The method of claim 10, wherein the volume of the sample is between about 30 μL and about 200 μL.

12. The method of claim 1, wherein the aptamer comprises a nucleic acid sequence that is specific for at least one tumor-specific biomarker.

13. The method of claim 1, wherein the reporter system further comprises:
2) a second distinct aptamer probe operably linked to a second distinct reporter pair that includes a second donor moiety operably linked to a second acceptor moiety, such that the second acceptor moiety silences the second donor moiety in its native, or inactive, state.

14. The method of claim 13, wherein the reporter system further comprises 3) a third distinct aptamer probe operably linked to a third distinct detectable label.

15. The method of claim 1, wherein the label is detected by flow cytometry, by immunophenotyping, by tissue immunohistochemical stain, by fluorescence microscopy, or by any combination thereof.

16. The method of claim 1, wherein the sample is contacted with the reporter system at about room temperature for about 20 to about 30 minutes.

17. A method for detecting a circulating tumor cell in a mammalian blood sample, comprising contacting the sample with a reporter system that comprises:
1) a first aptamer probe sequence that specifically targets a tumor-specific biomarker operably linked to a first reporter pair that includes a first donor moiety operably linked to a first acceptor moiety, such that the first acceptor moiety silences the first donor moiety in its native, or inactive, state,
under conditions effective, and for a time sufficient, to detect the circulating tumor cell in the mammalian blood sample, wherein the first aptamer probe sequence consists of the nucleic acid sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

18. The method of claim 17, wherein the sample consists essentially of a single drop of blood.

19. The of claim 17, wherein the circulating tumor cell can be detected in the sample following incubation of the sample and the reporter system at room temperature for not more than about 20 to about 30 minutes.

20. The method of claim 19, adapted and configured for large-scale, multi-well, microplate, or high-throughput analysis of a plurality of samples.

21. The method of claim 20, wherein the plurality of samples may be assayed simultaneously or sequentially via an automated, multi-well, microplate reader system.

22. The method of claim 17, wherein the aptamer probe is specific for a tumor cell-binding core sequence.

23. The method of claim 22, wherein the aptamer probe consists essentially of an about 34- to about 72-mer nucleic acid sequence that specifically binds to a CD30-expressing tumor cell.

24. A method for simultaneously detecting two or more distinct tumor cell types, or two or more distinct cancer-specific biomarkers in a mammalian blood sample, comprising contacting the sample with a reporter system that comprises:
1) a first aptamer probe sequence that specifically targets a first tumor cell type or a first cancer-specific biomarker operably linked to a first reporter pair that includes a first donor moiety operably linked to a first acceptor moiety, such that the first acceptor moiety silences the first donor moiety in its native, or inactive, state, and
2) a second aptamer probe sequence that specifically targets a second distinct tumor cell type or a second cancer-specific biomarker operably linked to a second distinct reporter pair that includes a second distinct donor moiety operably linked to a second distinct acceptor moiety, such that the second acceptor moiety silences the second donor moiety in its native, or inactive, state,
under conditions effective, and for a time sufficient, to detect the first and the second distinct tumor cell types or the first and the second distinct cancer-specific biomarkers in the mammalian blood sample, wherein the first aptamer probe sequence consists of the nucleic acid sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

25. The method of claim 24, wherein the sample is human blood, and the conditions effective, and the time sufficient for detection, include room temperature incubation for not more than about 20 to about 30 minutes.

26. The method of claim 24, wherein the volume of the mammalian blood sample is between about 10 μL and about 300 μL.

27. The method of claim 26, wherein the volume of the mammalian blood sample is between about 30 μL and about 200 μL.

28. The method of claim 24, wherein the mammalian blood sample consists essentially of a single drop of human blood.

* * * * *